United States Patent [19]

Omura et al.

[11] 4,390,547
[45] * Jun. 28, 1983

[54] 2,2-DIMETHYL-3-(SUBSTITUTED ETHYL)CYCLOPROPANE CARBOXYLATE PESTICIDAL COMPOSITIONS AND METHODS

[75] Inventors: Yoshiaki Omura, Okayama; Fumio Mori, Kurashiki; Yoshiji Fujita, Kurashiki; Takashi Nishida, Kurashiki; Yoshin Tamai, Kurashiki; Fumio Wada, Fukuoka; Kazuo Itoi, Kurashiki, all of Japan

[73] Assignee: Kuraray Co., Ltd., Kurashiki, Japan

[ * ] Notice: The portion of the term of this patent subsequent to Nov. 10, 1998, has been disclaimed.

[21] Appl. No.: 259,507

[22] Filed: May 1, 1981

Related U.S. Application Data

[63] Continuation of Ser. No. 923,542, Jul. 11, 1978, abandoned.

[51] Int. Cl.$^3$ .............................................. A01N 53/00
[52] U.S. Cl. ..................................... 424/304; 424/305
[58] Field of Search ............................... 424/304, 305

[56] References Cited

U.S. PATENT DOCUMENTS

| | | | |
|---|---|---|---|
| 3,652,652 | 3/1972 | Julia | 560/124 |
| 3,836,568 | 9/1974 | Higo | 560/124 |
| 4,299,839 | 11/1981 | Omura | 424/274 |

FOREIGN PATENT DOCUMENTS

| | | | |
|---|---|---|---|
| 2539895 | 3/1976 | Fed. Rep. of Germany . | |
| 2547510 | 4/1976 | Fed. Rep. of Germany | 560/124 |
| 51-59839 | 5/1976 | Japan . | |
| 51-146442 | 12/1976 | Japan . | |
| 52-14748 | 3/1977 | Japan . | |
| 52-14749 | 3/1977 | Japan . | |
| 52-78824 | 7/1977 | Japan . | |
| 52-83522 | 7/1977 | Japan . | |
| 52-102252 | 9/1977 | Japan . | |
| 52-125122 | 10/1977 | Japan . | |

*Primary Examiner*—Michael L. Shippen
*Attorney, Agent, or Firm*—Burns, Doane, Swecker & Mathis

[57] ABSTRACT

Novel pesticidal compositions are comprised of a 2,2-dimethyl-3-(substituted ethyl)cyclopropanecarboxylic acid ester as the active ingredient, said cyclopropanecarboxylate having the structural formula:

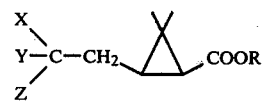

wherein X, Y and Z are the same or different and at least two of same are chlorine or bromine, with the remaining one being hydrogen, methyl, chlorine or bromine; R is an alcohol residue represented by one of the following structural formulae (II), (III), (IV) and (V):

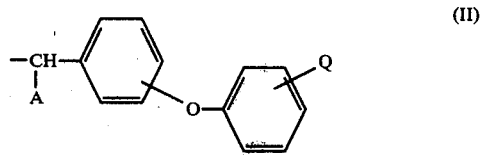

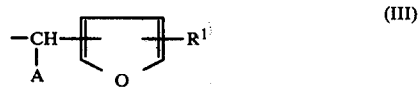

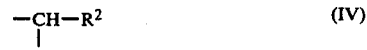

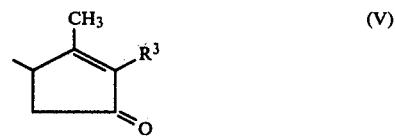

where A represents hydrogen, cyano, ethynyl or thiocarbamoyl; Q is hydrogen, chlorine, bromine, fluorine, methyl or trifluoromethyl; $R^1$ is propargyl or benzyl; $R^2$ represents 2-halogeno-3-phenyl-1-propen-1-yl, (dihalogenovinyloxy)phenyl, benzylphenyl, phthalimido, thiophthalimido, di- or tetrahydrophthalimido or dialkylmaleimido; $R^3$ represents allyl, 2,4-pentadienyl, propargyl or benzyl.

93 Claims, No Drawings

2,2-DIMETHYL-3-(SUBSTITUTED ETHYL)CYCLOPROPANE CARBOXYLATE PESTICIDAL COMPOSITIONS AND METHODS

This is a continuation of application Ser. No. 923,542, filed July 11, 1978, now abandoned.

BACKGROUND OF THE INVENTION

1. Field of the Invention

The present invention relates to certain novel pesticides and to novel pesticidal compositions comprising, as the active ingredient thereof, a 2,2-dimethyl-3-(substituted ethyl)cyclopropanecarboxylate having the structural formula:

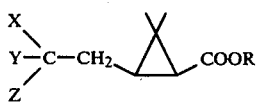

wherein X, Y and Z are the same or different and at least two of same are chlorine or bromine, with the remaining one being hydrogen, methyl, chlorine or bromine; R is an alcohol residue represented by one of the following structural formulae (II), (III), (IV) and (V):

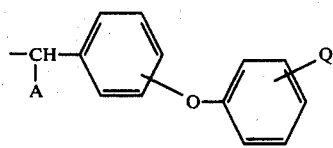

(II)

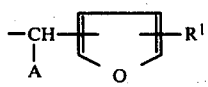

(III)

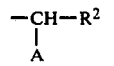

(IV)

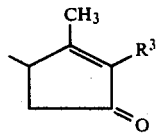

(V)

where A represents hydrogen, cyano, ethynyl or thiocarbamoyl; Q is hydrogen, chlorine, bromine, fluorine, methyl or trifluoromethyl; $R^1$ is propargyl or benzyl; $R^2$ represents 2-halogeno-3-phenyl-1-propen-1-yl, (dihalogenovinyloxy)phenyl, benzylphenyl, phthalimido, thiophthalimido, di- or tetrahydrophthalimido or dialkylmaleimide; $R^3$ represents allyl, 2,4-pentadienyl, propargyl or benzyl.

2. Description of the Prior Art

Since the discovery of BHC and DDT, there has been great development of a wealth of different insecticides containing, as the active ingredient thereof, a variety of organophosphorus compounds, carbamates, chlorinated organic compounds, and many others, for farming and gardening applications, and the use of such insecticides has resulted in marked increases in crop yields, thus enabling a stabilized supply of crops without depending upon climatic conditions. However, this success has been more or less offset by the fact that such agricultural and horticultural insecticides not only have high toxicity to humans and domesticated animals, but also same display a great tendency towards environmental pollution. Thus, the chronic toxicity and accumulation of such poisons have become a major contemporary concern. Furthermore, in many geographical areas, agricultural pests such as green rice leafhoppers, plant hoppers, etc., have been acquiring resistance to the common pesticides comprising the organic phosphorus compounds or the carbamates and the development of substitutes for such chemicals today is a pressing need. Pyrethroid pesticides, such as allethrin, phthalthrin, resmethrin, furamethrin, pyrethrin, etc., which have heretofore been employed for the purpose of controlling household pests are not only low in toxicity to man and domestic animals, have excellent pesticidal activities and are fast acting against noxious insects, but too are known for the fact that pests acquire resistance thereto only very rarely. However, because of their extremely low stability to light, their low residual activity and their high toxicity to fish, these compounds cannot be used as agricultural or horticultural pesticides to replace the organophosphorus or carbamate pesticides.

Under these circumstances, there have been certain developments in agricultural and horticultural pesticides which take advantage of the characteristics of pyrethroids, which characteristics are not possessed by the conventional agricultural pesticides.

Among the pesticides recently developed have been 3-phenoxybenzyl(+)-cis,trans-2,2-dimethyl-3-(2,2-dichlorovinyl)cyclopropanecarboxylate [Permethrin, U.S. Pat. No. 4,024,163] which has the structural formula:

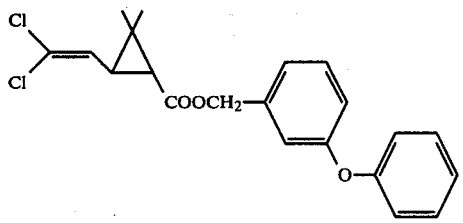

and 3-phenoxy-α-cyanobenzyl α-(4-chlorophenyl)isovalerate [Fenvalerate, U.S. Pat. No. 3,996,244] which has the structural formula:

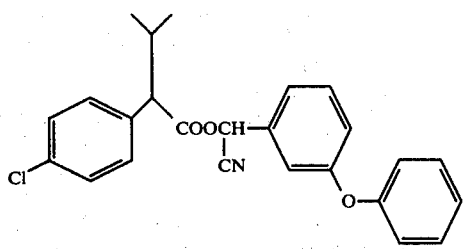

However, because of their high toxicity to fish, the applicability of these compounds is considerably restricted in geographical areas where, if used, they would contaminate the river water, etc.

SUMMARY OF THE INVENTION

Accordingly, a primary object of the present invention is to provide an agricultural pesticide having the characteristic properties of pyrethroids and yet displaying a higher residual activity than the pyrethroids.

Briefly, it has now surprisingly been determined that certain 2,2-dimethyl-3-(substituted ethyl)cyclopropanecarboxylic acid esters of the following structural formula (I) possess excellent pesticidal activity and high resistance to hydrolysis, and that the bulk of such compounds display markedly enhanced pesticidal activity, as well as excellent resistance to light and low toxicity to fish, as compared with the widely used allethrin:

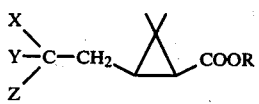
(I)

DETAILED DESCRIPTION OF THE INVENTION

In the above structural formula (I), X, Y and Z are the same or different and at least two of same are chlorine or bromine, with the remaining one being hydrogen, methyl, chlorine or bromine; R is an alcohol residue represented by one of the following structural formulae (II), (III), (IV) and (V):

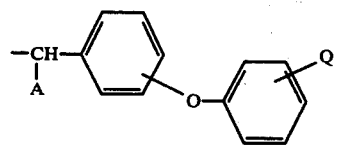
(II)

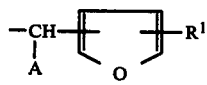
(III)

(IV)

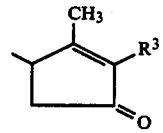
(V)

where A represents hydrogen, cyano, ethynyl or thiocarbamoyl; Q is hydrogen, chlorine, bromine, fluorine, methyl or trifluoromethyl; $R^1$ is propargyl or benzyl; $R^2$ represents 2-halogeno-3-phenyl-1-propen-1-yl, (dihalogenovinyloxy)phenyl, benzylphenyl, phthalimido, thiophthalimido, di- or tetrahydrophthalimido or dialkylmaleimido; $R^3$ represents allyl, 2,4-pentadienyl, propargyl or benzyl.

The group designated by R is exemplified by 3-phenoxybenzyl, 3-phenoxy-α-cyanobenzyl, 3-(4-chlorophenoxy)-α-cyanobenzyl, 3-(4-bromophenoxy)-α-cyanobenzyl, 3-(4-fluorophenoxy)-α-cyanobenzyl, 3-(4-methylphenoxy)-α-cyanobenzyl, 3-(3-trifluoromethylphenoxy)-α-cyanobenzyl, 3-phenoxy-α-ethynylbenzyl, 3-(4-chlorophenoxy)-α-ethynylbenzyl, 3-(4-bromophenoxy)-α-ethynylbenzyl, 3-(4-fluorophenoxy)-α-ethynylbenzyl, 3-(4-methylphenoxy)-α-ethynylbenzyl, 3-(3-trifluoromethylphenoxy)-α-ethynylbenzyl, 3-phenoxy-α-thiocarbamoylbenzyl, 4-phenoxybenzyl, 4-phenoxy-α-cyanobenzyl, 4-phenoxy-α-ethynylbenzyl, 2-phenoxybenzyl, 2-phenoxy-α-cyanobenzyl, 2-phenoxy-α-ethynylbenzyl, 5-propargyl-2-furylmethyl, 5-propargyl-2-(α-ethynylfurylmethyl), 5-benzyl-2-furylmethyl, 5-benzyl-3-furylmethyl, 5-benzyl-3-(α-cyanofurylmethyl), 5-benzyl-3-(α-ethynylfurylmethyl), 3-benzylbenzyl, 3-benzyl-α-cyanobenzyl, 3-benzyl-α-ethynylbenzyl, phthalimidomethyl, thiophthalimidomethyl, dihydrophthalimidomethyl, tetrahydrophthalimidomethyl, dimethylmaleimidomethyl, diethylmaleimidomethyl, 3-(2,2-dichlorovinyloxy)benzyl, 3-(2,2-dichlorovinyloxy)-α-cyanobenzyl, 3-chloro-4-phenyl-2-buten-1-yl, allethronyl, pyrethronyl, and the like.

The 2,2-dimethyl-3-(substituted ethyl)cyclopropanecarboxylic acid esters of structural formula (I) display excellent pesticidal activity against agricultural/horticultural pests such as paddy rice and other pests [e.g., rice stem borer (*Chilo suppressalis* WALKER), yellow rice borer (*Tryporyza incertulas* WALKER), pink borer (*Sesamia inferens* WALKER), white-backed plant hopper (*Sogatella furcifera* HORVATH), brown plant hopper (*Nilaparvata lugens* STÅL), small brown plant hopper (*Laodelphax striatellus* FALLEN), green rice leafhopper (*Nephotettix cincticeps* UHLER), zigzag-striped leafhopper (*Inazuma dorsalis* MOTSCHULSKY), rice leaf beetle, (*Oulema oryzae* KUWAYAMA), rice steam maggot (*Chlorops oryzae* MATSUMURA), rice leaf miner (*Agromyza oryzae* MUNAKATA), smaller rice leaf miner (*Hydrellia griseola* FALLÉN), paddy steam maggot (*Hydrellia sasakii* YUASA et ISHITANI), black rice bug (*Scotinophara lurida* BURMEISTER), rice stink bug (*Lagynotomus elongatus* DALLAS), corbett rice bug (*Leptocorixa corbetti* CHINA), southern green stink bug (*Nezara viridula* LINNÉ), rice plant skipper (*Parnara guttata* BREMER et GREY), grass leaf roller, (*Cnaphalocrocis medinalis* GUENEE), rice leaf roller (*Susumia exigua* BUTLER), rice green caterpillar (*Naranga aenescens* MOORE), armyworm (*Leucania separata* WALKER), northern cone-headed long-horn grasshopper (*Homorocoryphus jezoensis* MATSUMURA et al SHIRAKI)], field crop pests [e.g., winter grain mite (*Penthaleus major* DUGES), wireworm, wheat thigh chloropid fly (*Meromyza saltatrix* LINNE), leaf miner, wheat blossom midge (*Sitodiplosis mosellana* GEHIN), grain aphid (*Rhopalosiphum padi* LINNE), Japanese grain aphid (*Macrosiphum akebiae* SHINJI), corn leaf aphid (*Rhopalosiphum maidis* FITCH), corn borer (*Ostrinia furvacalis* GUENEE), sweet potato leaf folder (*Brachmia triannulella* HERRICH-SCHÄFFER), bindweed leaf miner (*Badellia sommulentella* ZELLER), sweet potato leaf worm (*Aedia leucomelas* LINNE), green peach aphid (*Myzus persicae* SULZER), cotton aphid (*Aphis gossypii* GLOVER), foxglove aphid (*Aulacorthum solani* KALTENBACH), large 28-spotted lady beetle (*Henosepilachna vigintioctomaculata* MOTSCHULSKY), 28-spotted lady beetle (*H. vigintioctopunctata* FABRICIUS), siebold's globular snail (*Acusta despecta* GRAY), false melon beetle (*Atrachya menetriesi* FALDERMANN), two-stripped leaf beetle (*Paraluperodes nigrobilineatus* MOTSCHULSKY), bean leaf beetle (*Colposcelis signata* MOTSCHULSKY), soybean root miner (*Melanagromyza dolichostigma* DE MEIJERE), soybean steam midge (*Profeltiella soya* MONZEN), soybean steam miner (*Melanagromyza sojae* ZEHNTNER), soybean aphid (*Aphis glycines* MATSUMURA), small bean bug (*Chauliops fallax* SCOTT), bean frosted weevil (*Eugnathus distinctus* ROELOFS), flax bud worm (*Heliothis viriplaca adaucta* BUTLER), tobacco striped caterpillar (*Pyrrhia umbra* HUFNAGEL), bean webworm (*Syllepte ruralis* SCOPLI), castaneous garden beetle (*Maladera castanea* ARROW), soybean bettle (*Anomala rufocuprea* MOTSCHULSKY), vegetable grasshopper (*P. sapporensis* SHIRAKI), bean blister beetle (*Epicauta gorhami* MARSEUL), soybean sawfly (*Takeuchiella pentagona* MALAISE), soybean pad gall midge (*Aspondylia sp.*), soybean pad borer (*Grapholitha glycinivorella* MATSUMURA), azuki pod worm (*Matsumuraeses phaseoli* MATSUMURA), lima bean pod borer (*Etiella-zinckenella* TREITSCHKE), bean bug (*Riptortus clavatus* THUNBERG), common green stink bug (*Nezara antennata* SCOTT), unibanded stink bug (*Piezodorus rubrofasciatus* FABRICIUS), sloe bug (*Dolycoris baccarum* LINNÉ), oriental tobacco bud worm (*Helicoverpa assulta* GUÉNEÉ), peppermint pyrausta (*Pyrausta aurata* SCOPOLI), peppermint leaf beetle (*Chrysolina exanthematica* WIEDEMANN), peacock butterfly, olive engraved weevil (*Hylobius cribripennis* MATSUMURA et KONO), lilac pyralid (*Margaronia nigropunctalis* BREMER), oriental chinch bug (*Cavelerius saccharivorus* OKAJIMA), sugarcane cottony aphid (*Ceratovacuna lanigera* ZEHNTNER), sugarcane shoot borer (*Eucosma schistaceana* SNELLEN)], vegetable pests [e.g., cabbage armyworm (*Mamestra brassicae* LINNÉ), tobacco cutworm (*Plodenia litura* FABRICIUS), common cutworm (*Agrotis fucosa* BUTLER), onion thrips (*Thrips tabaci* LINDEMAN), vegetable weevil (*Listroderes obliquus* KLUG), emma field cricket (*Teleogryllus emma* OHMACHI et MATSUURA), doenitz cricket (*Loxoblemmus doenitzi* STEIN), seed maggot (*Hylemya platura* MEIGEN), two-spotted spider mite (*Tetranychus urticae* KOCH), carmine mite (*Tetranychus telarius* LINNE), pill bug (*Armadillidium vulgare* LATREILLE), common cabbageworm (*Pieris rapae crucivora* BOISDUVAL), crucifer caterpillar (*Mesographe forficalis* LINNÉ), diamond-back moth (*Plutella maculipennis* CURTIS), cabbage aphid (*Brevicoryne brassicae* LINNÉ), cucurbit leaf beetle (*Aulacophora femoralis* MOTSCHULSKY), cotton caterpillar (*Margaronia indica* SAUNDERS), small green plant bug (*Lygus lucorum* MEYER-DÜR), onion maggot (*Hylemya antiqua* MEIGEN), stone leek leaf miner (*Phytobia cepae* HERING), stone leek miner (*Acrolepia alliella* SEMENOV ET KUZNETSOV), onion aphid (*Neotoxoptera formosana* TAKAHASHI)], orchard pests [e.g., arrowhead scale (*Unaspis yanonensis* KUWANA), california red scale (*Aonidiella aurantii* MASKELL), citrus leaf miner (*Phyllocnistis citrella* STAINTON), smaller citrus dog (*Papilio xuthus* LINNE), peach fruit moth (*Carposina niponensis* WALSINGHAM), oriental fruit moth (*Grapholitha molesta* BUSCK), summer fruit tortrix (*Adoxophyes orana* FISCHER VON RÖSLERSTAMM), gypsy moth (*Lymantria dispar* LINNE), tent caterpillar (*Malacosoma neustria testacea* MOTSCHULSKY), grape phylloxera (*Viteus vitifolii* FITCH), grape leafhopper (*Erythroneura apicalis* NAWA), grape whitefly (*Aleurolobus taonabae* KUWANA), small grape plume moth (*Stenoptilia vitis* SASAKI), persimmon fruit moth (*Stathmopoda flavofasciata* NAGANO), ume globose scale (*Eulecanium kunoense* KUWANA)], flowering plant pests [e.g., chrysanthemum aphid (*Macrosiphoniella sanborni* GILLETTE), narcissus bulb fly (*Lampetia equestris* FABRICIUS), rose aphid (*Macrosiphum ibarae* MATSUMURA), azalea lacewing bug (*Stephanitis pyrioides* SCOTT), fall webworm (*Hyphantria cunea* DRURY), fern scale (*Pinnaspis aspidistrae* SIGNORET), Japanese lawn grass cutworm (*Rusidrina depravata* BUTLER)], and cotton plant pests [e.g., boll weevil (*Anthonomus grandis* Boh.), pink bollworm (*Pectinophora gossypiella* Saund)] etc., as well as stored crop pests [e.g., rice weevil (*Sitophilus zeamais* MOTSCHULSKY), small rice weevil 8*Sitophilus oryzae* LINNÉ), lesser grain borer (*Rhizopertha dominica* FABRICIUS), azuki bean weevil (*Callosobruchus chinensis* LINNÉ)] and household pests [e.g., housefly (*Musca domestica vicina* MAQUANT), mosquito (*Culex pipiens*), cockroach (*Blattella germanica* LINNÉ)].

In regard to those 2,2-dimethyl-3-(substituted ethyl)-cyclopropanecarboxylic acid esters (I), of which optical isomers and/or stereoisomers exist, their activity is still further enhanced when these isomers are separated.

Among the subject 2,2-dimethyl-3-(substituted ethyl)cyclopropanecarboxylic acid esters (I), the substituted or unsubstituted 3-phenoxybenzyl ester of 2,2-dimethyl-3-(substituted ethyl)cyclopropanecarboxylic acid which has the structural formula (I'):

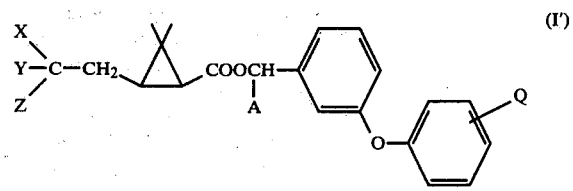

[wherein X, Y, Z, A and Q have the same meanings as above defined for structural formula (I)] is not only markedly lethal against the various pests mentioned hereinabove, but also displays high stability against light and low toxicity to fish. The substituted or unsubstituted 3-phenoxy-α-ethynylbenzyl ester of 2,2-dimethyl-3-(substituted ethyl)cyclopropanecarboxylic acid according to the invention which has the structural formula (I"):

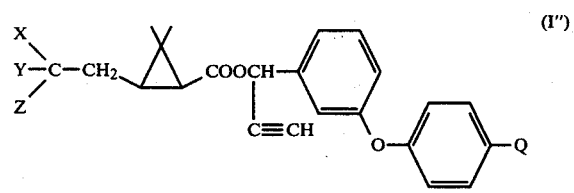

[wherein X, Y, Z and Q have the same meanings as above defined for structural formula (I)] and the substituted 3-phenoxy-α-cyanobenzyl ester of 2,2-dimethyl-3-(substituted ethyl)cyclopropanecarboxylic acid which has the structural formula (I'''):

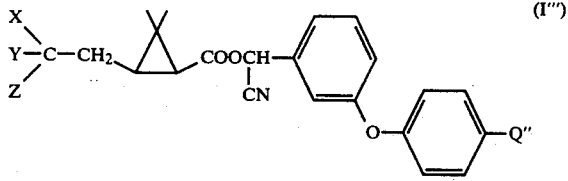

(I''')

[wherein X, Y and Z have the same meanings as above defined for structural formula (I); Q" represents chlorine, bromine, fluorine, methyl or trifluoromethyl] are the preferred pesticidal compounds because these compounds exhibit extremely low toxicity to fish, while at the same time are especially lethal. Stated differently, the above-mentioned esters are not only useful in a variety of applications, e.g., as household pesticides, stored crop pesticides and agricultural/horticultural pesticides, but are particularly useful as agricultural/horticultural pesticides intended for application to paddy fields and other areas where water drains into rivers.

To reiterate, the 2,2-dimethyl-3-(substituted ethyl)cyclopropanecarboxylic acid esters of the structural formula (I) are broad spectrum pesticides and are invariably low in toxicity to man and domestic animals. Moreover, the bulk of same area concomitantly low in toxicity to fish and highly resistant to light and hydrolysis, and, moreover, display high residual activity.

Furthermore, the 2,2-dimethyl-3-(substituted ethyl)-cyclopropanecarboxylic acid esters of the structural formula (I) are not only insecticidal, but also show promising repellent activity against mites and/or produce synergistic effects with other biologically active compounds. Thus, the compounds (I) can be made available at low cost as control agents against agricultural and horticultural insects, forest insects, insects injurious to harvested crops, household insects, and mites and other pests belonging to the following families: Tettigoniidae, Gryllidae, Gryllotalpidae, Blattidae, Reduviidae, Pyrrhocoridae, Cimicidae, Delphacidae, Aphididae, Diaspididae, Pseudococcidae, Scarabaeidae, Dermestidae, Coccinellidae, Tenebrionidae, Chrysomelidae, Bruchidae, Tineidae, Noctuidae, Lymantriidae, Pyralidae, Culicidae, Tipulidae, Stomoxydae, Trypetidae, Muscidae, Galliphoridae, Pulicidae, Tetranychidae and Dermanyssidae.

Compare further our pending Japanese application, Serial No. 304/76, filed Jan. 1, 1976, published July 12, 1977, hereby expressly incorporated by reference and relied upon.

The following is a representative list of certain preferred 2,2-dimethyl-3-(substituted ethyl)cyclopropanecarboxylic acid esters of the structural formla (I) according to this invention:

| Compound No. | Structural formula |
|---|---|
| (1) | 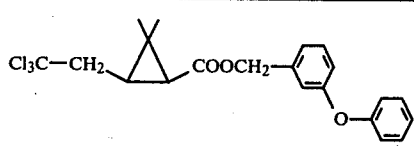<br>3-Phenoxybenzyl 2,2-dimethyl-3-(2,2,2-trichloroethyl) cyclopropanecarboxylate; |
| (2) | 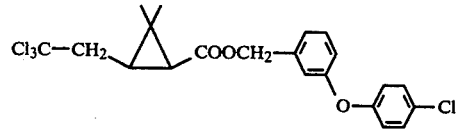<br>3-(4-Chlorophenoxy)benzyl 2,2-dimethyl-3-(2,2,2-trichloroethyl)cyclopropanecarboxylate; |
| (3) | 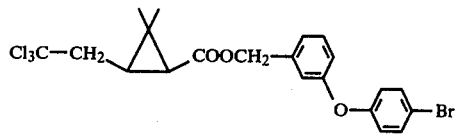<br>3-(4-Bromophenoxy)benzyl 2,2-dimethyl-3-(2,2,2-trichloroethyl)cyclopropanecarboxylate; |
| (4) | 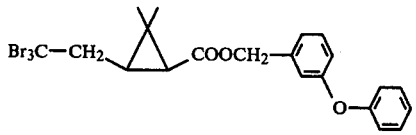<br>3-Phenoxybenzyl 2,2-dimethyl-3-(2,2,2-tribromoethyl) cyclopropanecarboxylate; |
| (5) | <br>3-Phenoxybenzyl 2,2-dimethyl-3-(2,2-dichloropropyl) cyclopropanecarboxylate; |
| (6) | <br>3-Phenoxybenzyl 2,2-dimethyl-3-(2,2-dibromoethyl) cyclopropanecarboxylate; |
| (7) | 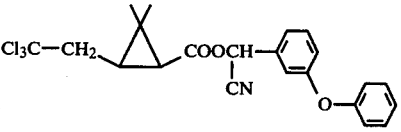<br>3-Phenoxy-α-cyanobenzyl 2,2-dimethyl-3-(2,2,2-trichloroethyl)cyclopropanecarboxylate; |
| (8) | 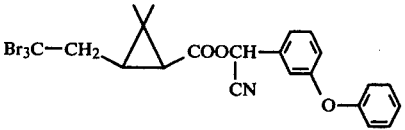<br>3-Phenoxy-α-cyanobenzyl 2,2-dimethyl-3-(2,2,2-tribromoethyl)cyclopropanecarboxylate; |

-continued

| Compound No. | Structural formula |
|---|---|
| (9) | 3-Phenoxy-α-cyanobenzyl 2,2-dimethyl-3-(2,2-dichloropropyl)cyclopropanecarboxylate; |
| (10) | 3-Phenoxy-α-cyanobenzyl 2,2-dimethyl-3-(2,2-dibromoethyl)cyclopropanecarboxylate; |
| (11) | 3-Phenoxy-α-ethynylbenzyl 2,2-dimethyl-3-(2,2,2-trichloroethyl)cyclopropanecarboxylate; |
| (12) | 3-Phenoxy-α-ethylnylbenzyl 2,2-dimethyl-3-(2,2,2-tribromoethyl)cyclopropanecarboxylate; |
| (13) | 3-Phenoxy-α-ethynylbenzyl 2,2-dimethyl-3-(2,2-dichloropropyl)cyclopropanecarboxylate; |
| (14) | 3-Phenoxy-α-ethynylbenzyl 2,2-dimethyl-3-(2,2-dibromoethyl)cyclopropanecarboxylate; |
| (15) | 3-(4-Chlorophenoxy)-α-cyanobenzyl 2,2-dimethyl-3-(2,2,2-trichloroethyl)cyclopropanecarboxylate; |
| (16) | 3-(4-Chlorophenoxy)-α-cyanobenzyl 2,2-dimethyl-3-(2,2,2-tribromoethyl)cyclopropanecarboxylate; |
| (17) | 3-(4-Bromophenoxy)-α-cyanobenzyl 2,2-dimethyl-3-(2,2,2-trichloroethyl)cyclopropanecarboxylate; |
| (18) | 3-(4-Fluorophenoxy)-α-cyanobenzyl 2,2-dimethyl-3-(2,2,2-trichloroethyl)cyclopropanecarboxylate; |
| (19) | 3-(4-Methylphenoxy)-α-cyanobenzyl 2,2,-dimethyl-3-(2,2,2-trichloroethyl)cyclopropanecarboxylate; |
| (20) | 3-(3-Trifluoromethylphenoxy)-α-cyanobenzyl 2,2-dimethyl-3-(2,2,2-trichloroethyl)cyclopropanecarboxylate; |
| (21) | 3-(4-Chlorophenoxy)-α-ethynylbenzyl 2,2-dimethyl-3-(2,2,2-trichloroethyl)cyclopropanecarboxylate; |
| (22) | 3-(4-Bromophenoxy)-α-ethynylbenzyl 2,2-dimethyl-3-(2,2,2-trichloroethyl)cyclopropanecarboxylate; |

| Compound No. | Structural formula |
|---|---|
| (23) | 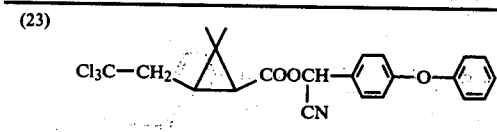 4-Phenoxy-α-cyanobenzyl 2,2-dimethyl-3-(2,2,2-trichloroethyl)cyclopropanecarboxylate; |
| (24) | 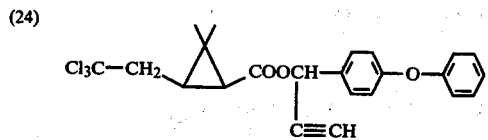 4-Phenoxy-α-ethynylbenzyl 2,2-dimethyl-3-(2,2,2-trichloroethyl)cyclopropanecarboxylate; |
| (25) | 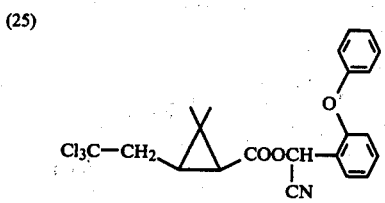 2-Phenoxy-α-cyanobenzyl 2,2-dimethyl-3-(2,2,2-trichloroethyl)cyclopropanecarboxylate; |
| (26) | 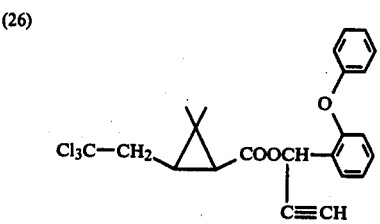 2-Phenoxy-α-ethynylbenzyl 2,2-dimethyl-3-(2,2,2-trichloroethyl)cyclopropanecarboxylate; |
| (27) | 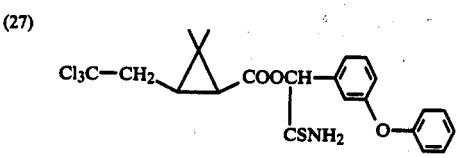 3-Phenoxy-α-thiocarbamoylbenzyl 2,2-dimethyl-3-(2,2,2-trichloroethyl)cyclopropanecarboxylate; |
| (28) | 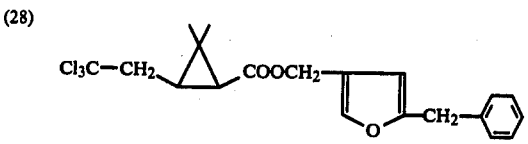 5-Benzyl-3-furylmethyl 2,2-dimethyl-3-(2,2,2-trichloroethyl)cyclopropanecarboxylate; |
| (29) | 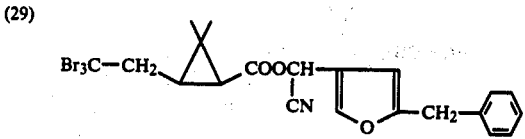 5-Benzyl-3-(α-cyanofurylmethyl) 2,2-dimethyl-3-(2,2,2-tribromoethyl)cyclopropanecarboxylate; |
| (30) | 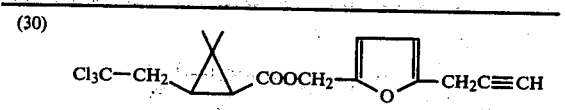 5-Propargyl-2-furylmethyl 2,2-dimethyl-3-(2,2,2-trichloroethyl)cyclopropanecarboxylate; |
| (31) | 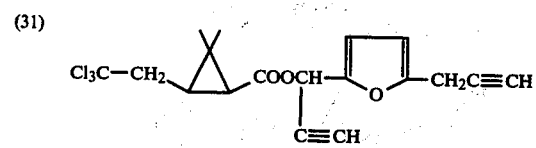 5-Propargyl-2-(α-ethynylfurylmethyl) 2,2-dimethyl-3-(2,2,2-trichloroethyl)cyclopropanecarboxylate; |
| (32) | 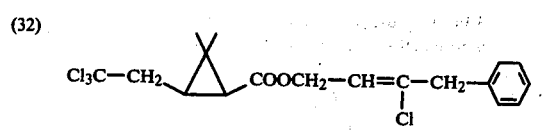 3-Chloro-4-phenyl-2-butenyl 2,2-dimethyl-3-(2,2,2-trichloroethyl)cyclopropanecarboxylate; |
| (33) | 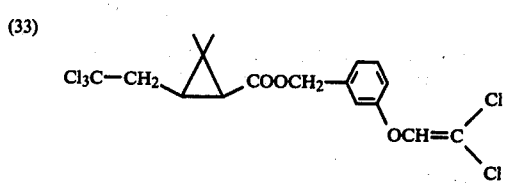 3-(2,2-dichlorovinyloxy)benzyl 2,2-dimethyl-3-(2,2,2-trichloroethyl)cyclopropanecarboxylate; |
| (34) | 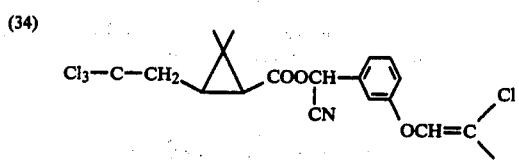 3-(2,2-dichlorovinyloxy)-α-cyanobenzyl 2,2-dimethyl-3-(2,2,2-trichloroethyl)cyclopropanecarboxylate; |
| (35) | 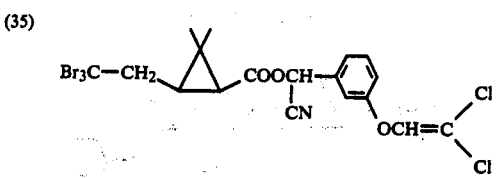 3-(2,2-dichlorovinyloxy)-α-cyanobenzyl 2,2-dimethyl-3-(2,2,2-tribromoethyl)cyclopropanecarboxylate; |
| (36) | 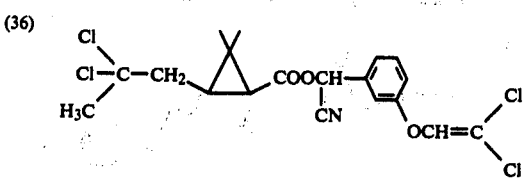 3-(2,2-dichlorovinyloxy)-α-cyanobenzyl 2,2-dimethyl-3-(2,2-dichloropropyl)cyclopropanecarboxylate; |

| Com- pound No. | Structural formula |
|---|---|
| (37) | 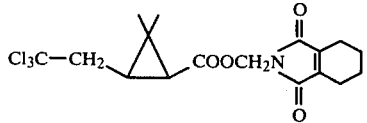<br>3,4,5,6-Tetrahydrophthalimidomethyl 2,2-dimethyl-3-(2,2,2-trichloroethyl)cyclopropanecarboxylate; and |
| (38) | 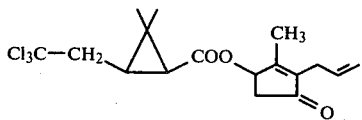<br>Allethronyl 2,2-dimethyl-3-(2,2,2-trichloroethyl) cyclopropanecarboxylate. |

The method for producing the 2,2-dimethyl-3-(substituted ethyl)cyclopropanecarboxylic acid esters which have the structural formula (I) will now be described:

Among the lower alkyl esters of 2,2-dimethyl-3-(substituted ethyl)cyclopropanecarboxylic acids which are convenient intermediates for the production of said 2,2-dimethyl-3-(substituted ethyl)cyclopropanecarboxylic acid esters according to the invention, the lower alkyl esters of 2,2-dimethyl-3-(2,2,2-trihalogenoethyl)-cyclopropanecarboxylic acids have been reported and can be easily produced by one of the alternative processes (i) and (ii) schematically shown below [published, unexamined Japanese patent applications Nos. 59839/76, filed Oct. 23, 1974, published May 25, 1976 (Sankyo Co., Ltd.), 146442/76, filed June 10, 1975, published Dec. 16, 1976 (assigned to the assignee hereof), and 78824/77, filed Dec. 26, 1975, published July 2, 1977 (Sagami Chemical Research Center)]:

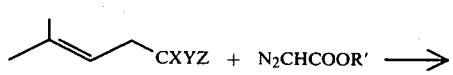  (i)

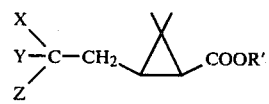

  (ii)

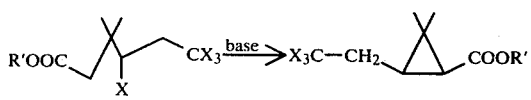

(wherein X, Y and Z are the same or different and each represents chlorine or bromine; R' is a lower alkyl, e.g., $C_1$–$C_5$, group)

The lower alkyl ($C_1$–$C_5$) esters of 2,2-dimethyl-3-(2,2-dihalogenoethyl)cyclopropanecarboxylic acids and the lower alkyl esters of 2,2-dimethyl-3-(2,2-dihalogeno-2-methyl-ethyl)cyclopropanecarboxylic acids are novel compounds and can be produced by the same procedure (iii) as the above process (ii) except that 1,1,1-trihalogenomethane or 1,1,1-trihalogenoethane is used in lieu of tetrahalogenomethane, viz.:

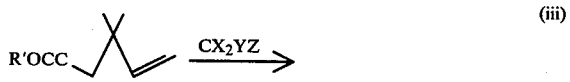  (iii)

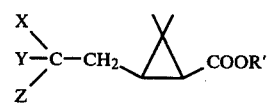

(wherein X and Y are the same or different and each represents chlorine or bromine; Z represents hydrogen or methyl; R' represents a lower alkyl group)

The lower alkyl ester of 2,2-dimethyl-3-(substituted ethyl)cyclopropanecarboxylic acid obtained by any of the above methods (i) to (iii) is readily converted to a 2,2-dimethyl-3-(substituted ethyl)cyclopropanecarboxylic acid ester of structural formula (I) by the following procedure:

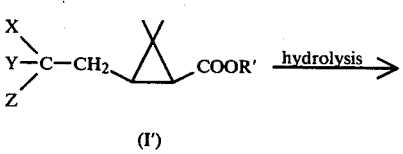

(I')

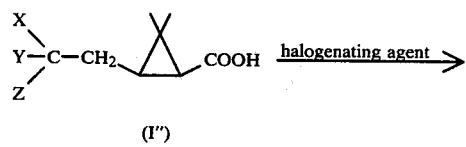

(I")

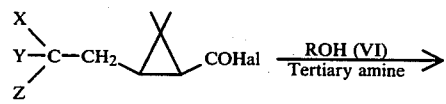

(I''')

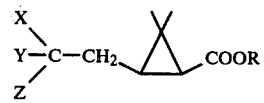

(I)

(wherein X, Y Z and R have the same meanings as above defined for structural formula (I); R' represents lower alkyl; Hal denotes halogen)

Thus, the compound of structural formula (I') is hydrolyzed to the free carboxylic acid (I") in conventional manner and the latter acid (I") is treated with a halogenating agent, such as thionyl chloride, thionyl bromide, phosphorus trichloride, phosphorus tribromide, phosphorus oxychloride, phosphorus pentachloride, or the like, to obtain the corresponding carboxylic acid halide (I'''). This carboxylic acid halide (I''') is then reacted with an alcohol of structural formula (VI) in the presence of a tertiary amine, such as pyridine or triethylamine. By the above steps, there is conveniently obtained a 2,2-dimethyl-3-(substituted ethyl)cyclopropanecarboxylic acid ester of the structural formula (I). For the production of the 2,2-dimethyl-3-(substituted ethyl)cyclopropanecarboxylic acid ester (I) from the compound of structural formula (I′), or the free carboxylic acid of structural formula (I″), there are several alternative known processes in addition to the above acid halide esterification process now designated as (a). Thus, (b) the transesterification process in which a compound of structural formula (I′) is directly reacted with an alcohol (VI) in an inert solvent and in the presence of sodium hydride or alkali metal alkoxide, (c) the esterification process wherein said free carboxylic acid (I″) is reacted with an alcohol (VI) in an inert solvent and in the presence of a dehydrative condensing agent such as dicyclohexylcarbodiimide, (d) the esterification process in which an acid anhydride of free carboxylic acid (I″) is reacted with an alcohol (VI), and (e) the esterification process in which an alkali metal salt, silver salt or organic tertiary base salt of free carboxylic acid (I″) is reacted with a halide of alcohol (VI) may be mentioned as representative examples. In addition, (f) among the 2,2-dimethyl-3-(substituted ethyl)cyclopropanecarboxylic acid esters of structural formula (I), those esters comprising α-cyano-substituted benzyl-type alcohol residues can be easily produced by the procedure schematically shown below:

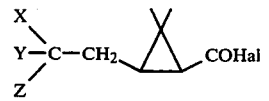

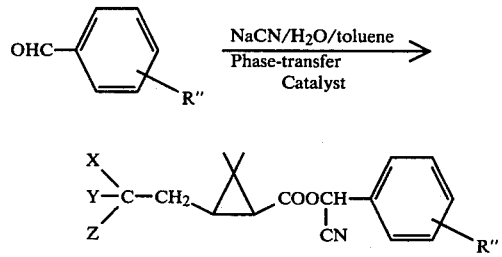

[wherein X, Y and Z have the same meanings as above defined for structural formula (I); R″ represents

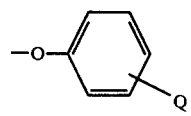

2,2-dihalogenovinyloxy or benzyl where Q has the meaning as above defined for structural formula (I)].

Further, as reflected in published Japanese patent application, Serial No. 125122/77, published Oct. 20, 1977 (assigned to the assignee hereof), the 2,2-dimethyl-3-(substituted ethyl)cyclopropanecarboxylic acid ester having the structural formula (I) can also be easily produced by the procedure schematically shown below:

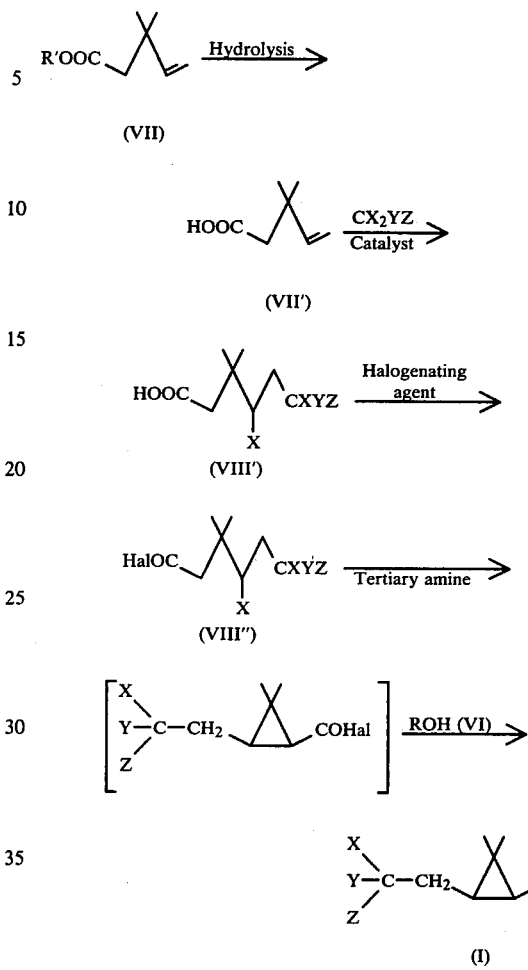

(wherein X, Y and Z are the same or different and X and Y are respectively chlorine or bromine with Z representing hydrogen, methyl, chlorine or bromine; R has the same meaning as above defined for structural formula (I); R′ represents a lower alkyl group; Hal denotes halogen)

Thus, the compound of structural formula (VII) is hydrolyzed in conventional manner to the free carboxylic acid (VII′) which is reacted with a tetrahalogenomethane or 1,1,1-trihalogenoethane in the presence of a radical initiator, or a transition metal salt-amine catalyst, to prepare a compound of structural formula (VIII′) which, in turn, is treated with a halogenating agent, such as thionyl chloride, thionyl bromide, phosphorus trichloride, phosphorus tribromide, phosphorus oxychloride, phosphorus pentachloride, or the like, to prepare the corresponding carboxylic acid halide (VIII″). This carboxylic acid halide (VIII″) is treated with a tertiary amine, such as pyridine, triethylamine, or the like, and, then, an alcohol of structural formula (VI) is reacted with the resulting reaction mixture. By the above procedure there can be obtained the desired 2,2-dimethyl-3-(substituted ethyl)cyclopropanecarboxylic acid ester having the structural formula (I).

The 2,2-dimethyl-3-(substituted ethyl)cyclopropanecarboxylic acid ester of structural formula (I) according to the invention (hereinafter referred to as the "active" compound) can be used in the form of conventional formulations, such as solutions, emulsifiable concentrates, wettable powders, suspensions, dusts, granules, microfine granules, powders, coatings, aerosols, mosquito incense coils, fumigants, slow-acting or delayed release fumigants, electric mosquito incense mats, capsules, and so forth. These formulations may be prepared by conventional procedures, for example, by admixing the active compound with a volume builder, such as a liquid, solid or liquefied gas diluent or carrier (optionally with a surfactant, i.e., an emulsifier, and/or a dispersing agent, and/or a foaming agent). Where water is employed as the volume builder or diluent, an organic solvent may be employed as a co-solvent.

Suitable liquid diluents or carriers usually include aromatic hydrocarbons, such as xylene, toluene, benzene, alkylnaphthalene, etc.; chlorinated aromatic or aliphatic hydrocarbons, such as chlorobenzene, chloroethylene, methylene chloride, etc.; aliphatic or alicyclic hydrocarbons, such as cyclohexane, paraffin (e.g., mineral oil distillate); alcohols, such as butanol, glycol and its usual ether and ester; ketones, such as acetone, methyl ethyl ketone, methyl isobutyl ketone, cyclohexanone, etc.; highly polar solvents, such as dimethylformamide, dimethylsulfoxide, acetonitrile, etc.; and water.

By "liquefied gas diluent or carrier" there is intended a liquid which is gaseous at normal temperature and pressure, such as aerosol propellants, e.g., dichlorodifluoromethane, trichlorofluoromethane, etc.

Preferred examples of said solid diluent or carrier are finely divided, naturally occurring minerals such as kaolin, clay, talc, chalk, quartz, attapulgite, montmorillonite, diatomaceous earth, etc.; and finely divided synthetic minerals, such as alumina, silicates, etc.

As preferred examples of said emulsifiers and foaming agents there are mentioned nonionic and anionic emulsifying agents, such as polyoxyethylene-aliphatic carboxylic acid esters; polyoxyethylene-aliphatic alcohol ethers, such as alkyl aryl polyglycol ether; alkylsulfonates, alkylsulfates, arylsulfonates and albumin hydrolysate. Preferred examples of the dispersing agents include spent lignosulfite liquor and methyl-cellulose.

Adhesive agents, such as carboxymethyl-cellulose; powdery, granular or latex-type naturally occurring or synthetic high molecular weight compounds, such as gum Arabic, polyvinyl alcohol, polyvinyl acetate, etc., may be employed in the preparation of said formulations. In addition, colorants such as inorganic pigments, e.g., iron oxide, titanium oxide, etc.; and organic dyestuffs, e.g., alizarin dyes, azo dyes, phthalocyanine dyes, etc., too may be incorporated in the subject formulations.

The pesticidal activity of the active compound according to this invention can be further improved by the addition of synergists, such as N-octylbicycloheptene dicarboximide and alkyl aryl sulfonate (trademark MGK-5026), octachloro dipropyl ether, piperonyl butoxide, etc. The stability of the above-mentioned active compound which is an active ingredient of these pesticidal formulations can be increased by the addition of an antioxidant of the phenol, amine or other type, such as 2,6-di-t-butyl-4-methylphenol (BHT), 2,6-di-t-butylphenol, etc.

Insecticidal compositions or formulations having yet further improved activity may be obtained by using the active compound of this invention in combination with other pesticides. Among such "other" pesticides are chlorinated organic pesticides such as DDT, BHC, Methoxychlor, etc., carbamates such as Tsumacide[m-tolyl methylcarbamate], carbaryl[1-naphthyl N-methylcarbamate], 3,4-dimethylphenyl N-methylcarbamate, 3,5-dimethylphenyl N-methylcarbamate, 2-isopropoxyphenyl N-methylcarbamate, etc.; organophosphorus compounds such as O,O-dimethyl-O-(3-methyl-4-nitrophenyl)phosphorothionate, DDVP [O,O-dimethyl-O-(2,2-dichlorovinyl)phosphate], diazinon[diethyl 2-isopropyl-4-methyl-6-pyrimidinyl phosphorothionate], phenthion, O,O-dimethyl-O-4-cyanophenyl phosphorothionate, O,O-dimethyl-S-[α-(ethoxycarbonyl)benzyl]phosphorodithioate, 2-methoxy-4H-1,3,2-benzodioxaphosphorin-2-sulfide, O-ethyl-O-4-cyanophenyl phenylphosphorothionate, malathion[S-1,2-bis(ethoxycarbonyl)ethyl dimethyl phosphorothiolothionate], etc.; cyclopropanecarboxylic acid esters such as pyrethrin, allethrin, N-(3,4,5,6-tetrahydrophthalimido)-methyl chrysanthemate (tetramethrin), 5-benzyl-3-furylmethyl chrysanthemate (resmethrin), 5-propargylfurfuryl chrysanthemate (furamethrin), 5-propargyl-2-methyl-3-furylmethyl chrysanthemate (proparthrin), 3-phenoxybenzyl chrysanthemate(phenothrin), 3-phenoxy-α-ethynylbenzyl chrysanthemate, 3-phenoxybenzyl 2,2-dimethyl-3-(2,2-dichlorovinyl)cyclopropanecarboxylate(permethrin), 3-phenoxy-α-ethynylbenzyl 2,2-dimethyl-3-(2,2-dichlorovinyl)cyclopropanecarboxylate, 3-phenoxy-α-cyanobenzyl 2,2-dimethyl-3-(2,2-dichlorovinyl)cyclopropanecarboxylate (cypermethrin), etc.; and substituted acetic acid esters such as 3-phenoxy-α-cyanobenzyl α-(4-chlorophenyl)isovalerate, 3-phenoxy-α-ethynylbenzyl α-(4-chlorophenyl)isovalerate, etc.

In each formulation, the active compound is generally incorporated in an amount ranging from 0.01 to 95 weight percent preferably from about 0.1 to 90 weight percent.

The active compound of this invention can be used in any of the aforementioned varied types of formulations or as further formulated into various application forms. The content of the active compound in any such application form may be varied over a broad range. The concentration of active compound in such an application form may range from 0.0000001 to 100 weight percent, preferably from about 0.001 to 10 weight percent.

The pesticides containing any of the active compounds according to this invention are conveniently utilized by routine procedures suited to individual modes of application.

The following examples of synthesis, test examples, formulation examples and utility examples are further illustrative of this invention, and are nowise intended as limitative. In the formulation examples and utility examples, all parts are by weight. The compound numbers correspond to the 2,2-dimethyl-3-(substituted ethyl)cyclopropanecarboxylic acid esters (1) to (38) of the aforenoted structural formula (I).

SYNTHESIS EXAMPLE 1

Into 50 ml of water were dissolved 11.0 g of sodium hydroxide, followed by the addition of 50.0 g of ethyl cis, trans-2,2-dimethyl-3-(2,2,2-trichloroethyl) cyclopropanecarboxylate and about 100 ml of ethanol as a solvent. This mixture was stirred at room temperature for one day. To the reaction mixture was further added a solution of 8.0 g sodium hydroxide in 15 ml of water and the mixture was stirred at room temperature for two days. The resultant reaction mixture was distilled under reduced pressure to remove ethanol and extracted with diethyl ether to recover the unreacted ethyl cis, trans-2,2-dimethyl-3-(2,2,2-trichloroethyl) cyclopropanecarboxylate. Then, the alkaline aqueous layer was acidified by the addition of hydrochloric acid and extracted with diethyl ether. The etheral layer was dried over anhydrous magnesium sulfate and distilled to remove diethyl ether. By the above procedure there were obtained 45.2 g of cis, trans-2,2-dimethyl-3-(2,2,2-trichloroethyl) cyclopropanecarboxylic acid. To 45.2 g of the carboxylic acid were added 131 g of thionyl chloride and 150 g of benzene and the mixture was heated under reflux overnight. The reaction mixture was then distilled under reduced pressure to remove the low-boiling fraction. The resultant residue was purified by distillation under reduced pressure to obtain 37.2 g of cis, trans-2,2-dimethyl-3-(2,2,2-trichloroethyl) cyclopropanecarboxylic acid chloride which displayed the following NMR spectrum [yield 77% based on the ethyl cis, trans-2,2-dimethyl-3-(2,2,2-trichloroethyl) cyclopropanecarboxylate].

NMR spectrum (60 MHz) $\delta_{TMS}^{CDCl_3}$: 1.27, 1.31, 1.33 (each s) 6H; 1.63–2.42 (m) 2H; 2.66–3.13 (m) 2H.

Into 50 ml of dry benzene were dissolved 5.3 g of cis, trans-2,2-dimethyl-3-(2,2,2-trichloroethyl) cyclopropanecarboxylic acid chloride, followed by the addition of 4.5 g of 3-phenoxy-α-cyanobenzyl alcohol and 4.7 g of pyridine. The mixture was stirred at room temperature overnight. The reaction mixture was diluted with diethyl ether, washed with water and dilute hydrochloric acid, dried over anhydrous magnesium sulfate and distilled to remove the low-boiling fraction. The resultant oily residue was purified by preparative liquid chromatography (Waters Associates, Prep LC/System 500, diethyl ether/n-hexane=4:96 v/v) to obtain 8.2 g of 3-phenoxy-α-cyanobenzyl cis, trans-2,2-dimethyl-3-(2,2,2-trichloroethyl) cyclopropanecarboxylate [Compound (7)] (yield: 90%). The cis- and trans-isomers were separated from each other by the above preparative liquid chromatography. The NMR spectra of these isomers are shown below.

NMR spectrum (90 MHz) $\delta_{HMS}^{CDCl_3}$: Cis-isomer: 1.19, 1.21, 1.25, 1.28 (each s) 6H; 1.38–1.83(m) 2H; 2.73–3.29(m) 2H; 6.36(s) 1H; 6.90–7.50(m) 9H. Trans-isomer: 1.10, 1.13, 1.23 (each s) 6H; 1.46(d) 1H; 1.58–1.93(m) 1H; 2.38–2.97(m) 2H; 6.31, 6.33 (each s) 1H; 6.82–7.46(m) 9H.

SYNTHESIS EXAMPLES 2 TO 6

The procedure of Synthesis Example 1 was repeated, except that 3-(4-chlorophenyl) benzyl alcohol, 3-(4-bromophenoxy) benzyl alcohol, 5-benzyl-3-furylmethyl alcohol, 3,4,5,6-tetrahydrophthalimidomethyl alcohol or allethrolone was used, respectively, in lieu of 3-phenoxy-α-cyanobenzyl alcohol. By these procedures there were obtained the corresponding cis, trans-2,2-dimethyl-3-(2,2,2-trichloroethyl) cyclopropanecarboxylic acid esters [Compounds (2), (3), (28), (37) and (38)], respectively in a not less than 90% yield. By preparative liquid chromatography, the cis- and trans-isomers, as well as a mixture thereof, were obtained. The NMR spectra of the carboxylic acid esters obtained above are shown in Table 1.

TABLE 1

| Compound No. | | NMR spectrum (90 MHz) $\delta_{HMS}^{CDCl_3}$: |
|---|---|---|
| (2) | Cis-isomer | 1.24(s)6H; 1.38–1.83(m)2H; 2.98(dd), 3.20(dd)2H; 5.07(s)2H; 6.84–7.46(m)8H |
| | Trans-isomer | 1.17, 1.23(each s)6H; 1.48(d)1H; 1.78(q)1H; 2.61(dd), 2.85(dd)2H; 5.07(s)2H; 6.77–7.45(m)8H |
| (3) | Cis-isomer | 1.18(s)6H; 1.31–1.74(m)2H; 2.89(dd), 3.13(dd)2H; 5.00(s)2H; 6.70–7.46(m)8H |
| | Trans-isomer | 1.14, 1.21(each s)6H; 1.46(d)1H; 1.76(q)1H; 2.58(dd), 2.82(dd)2H; 5.05(s)2H; 6.70–7.48(m)8H |
| (28) | Mixture | 1.19, 1.22, 1.24, 1.26(each s)6H; 1.36–1.93(m)2H; 2.50–3.33(m)2H; 3.94(s)2H; 4.89, 4.94(each s)2H; 6.02(s)1H; 7.28(s), 7.35(s)6H |
| (37) | Mixture | 1.20, 1.22, 1.25, 1.28(each s)6H; 1.35–1.98(m)6H; 2.20–2.50(m)4H; 2.53–3.32(m)2H; 5.30–5.74(m)2H |
| (38) | Cis-isomer | 1.19, 1.20(each s)6H; 1.35–1.82(m)2H; 1.82–3.30(m), 1.95, 1.96(each s)9H; 4.78–5.07(m)2H; 5.47–5.94(m)2H |
| | Trans-isomer | 1.18, 1.23(each s)6H; 1.48(d), 1.50(d)1H; 1.74(q)1H; 1.86–3.14(m), 1.95(s)9H; 4.78–5.07(m)2H; 5.47–5.94(m)2H |

SYNTHESIS EXAMPLE 7

A pressure-resistant tubular reactor was charged with a mixture of 62.4 g of ethyl 3,3-dimethyl-4-pentenoate, 160 g of 1,1,1-trichloroethane and 4.7 g of t-butyl perbenzoate and, after the reactor was sealed, the contents were heated overnight at a temperature of 150° to 160° C. in an oil bath. Thereafter, the reaction mixture was distilled to recover the unreacted 1,1,1-trichloroethane and ethyl 3,3-dimethyl-4-pentenoate and further subjected to distillation under reduced pressure. By the above procedure there were obtained 15.0 g of ethyl 3,3-dimethyl-4,6,6-trichloroheptanoate having the following NMR spectrum (yield: 13%).

NMR spectrum (100 MHz) $\delta_{TMS}^{CCl_4}$: 1.04(s), 1.12(s), 1.17(t, J=7.5 Hz)9H; 2.16(d, J=15 Hz), 2.18(s), 2.47(dd, J=16 Hz and 7.5 Hz); 2.48(d, J=15 Hz), 2.89(dd, J=16 Hz and 1.5 Hz)7H; 4.03(q, J=7.5 Hz), 4.50(dd, J=7.5 Hz and 1.5 Hz)3H.

Into 50 ml of dry ethanol were dissolved 2.3 g of sodium metal and the ethanol solution was heated at 50° C., followed by the dropwise addition of 10.0 g of the ethyl 3,3-dimethyl-4,6,6-trichloroheptanoate. The mixture was heated under reflux for one hour. After cooling, the reaction mixture was acidified by the addition of a solution of hydrogen chloride in dry ethanol and distilled under reduced pressure to remove the ethanol. The residue was diluted with water and extracted with diethyl ether. The etheral layer was dried over anhydrous magnesium sulfate and distilled to remove the low-boiling fraction. By the above procedure there were obtained 7.4 g of crude ethyl cis, trans-2,2-dimethyl-3-(2,2-dichloropropyl) cyclopropanecarboxylate. Into a mixture of 5 g of water and 10 ml of ethanol were dissolved 2.3 g of sodium hydroxide, and to the above solution were added 7.4 g of the crude ethyl cis, trans-2,2-dimethyl-3-(2,2-dichloropropyl) cyclopropanecarboxylate obtained above. The mixture was stirred at a temperature of 40° to 65° C. overnight. The reaction mixture was then distilled under reduced pressure to remove the ethanol and extracted with diethyl ether to recover the unreacted ethyl cis, trans-2,2-dimethyl-3-(2,2-dichloropropyl) cyclopropanecarboxylate. Then, the alkaline aqueous layer was acidified by the addition of hydrochloric acid and extracted with diethyl ether. By the above procedure there were obtained 4.2 g of crude cis, trans-2,2-dimethyl-3-(2,2-dichloropropyl) cyclopropanecarboxylic acid.

To 4.2 g of crude cis, trans-2,2-dimethyl-3-(2,2-dichloropropyl) cyclopropanecarboxylic acid were added 9 g of thionyl chloride and 10 g of benzene, and the mixture was heated under reflux overnight. The reaction mixture was then distilled under reduced pressure to remove the low-boiling fraction and recover 4.5 g of crude 2,2-dimethyl-3-(2,2-dichloropropyl) cyclopropanecarboxylic acid chloride. In 30 ml of dry benzene were dissolved 2.4 g of the crude cis, trans-2,2-dimethyl-3-(2,2-dichloropropyl) cyclopropanecarboxylic acid chloride. To the benzene solution were added 2.0 g of 3-phenoxybenzyl alcohol, followed by the dropwise addition of 2.4 g of pyridine and the mixture was stirred at room temperature overnight. Thereafter, the reaction mixture was treated by the same procedure described in Synthesis Example 1 and the resulting oily residue was purified by the preparative liquid chromatography to obtain 2.1 g of 3-phenoxybenzyl cis, trans-2,2-dimethyl-3-(2,2-dichloropropyl) cyclopropanecarboxylate [Compound (5)]. By the above preparative liquid chromatography, the cis- and trans-isomers were separated from each other. The NMR spectra of these isomers are shown below.

NMR spectrum (100 MHz) $\delta_{TMS}^{CCl_4}$: Cis-isomer: 1.0, 1.12(each s)6H; 1.26–1.76(m)2H; 1.96(s)3H; 2.35(dd), 2.55(dd)2H; 4.86(s)2H; 6.64–7.24(m)9H. Trans-isomer: 1.06, 1.12(s)6H; 1.27(d), 1.54(q)2H; 2.01(s), 2.10(dd), 2.32(dd)5H; 4.90(s)2H; 6.66–7.24(m)9H.

SYNTHESIS EXAMPLE 8

Into 7.5 ml of water were dissolved 1.8 g of sodium cyanide and 0.09 g of benzyltriethylammonium chloride. To the solution was added a solution of 4.4 g of 3-(2,2-dichlorovinyloxy) benzaldehyde in 5.0 g of toluene and the mixture was stirred for 30 minutes. Then, a solution of 6.9 g of cis, trans-2,2-dimethyl-3-(2,2,2-trichloroethyl) cyclopropanecarboxylic acid chloride in 10 g of toluene was added dropwise over a period of about 30 minutes to the above solution. The mixture was further stirred at room temperature overnight and 6 g of water were then added to the mixture. The resultant toluene layer was washed with saturated sodium chloride solution and distilled under reduced pressure to remove toluene. The resulting oily residue was purified by preparative liquid chromatography to obtain 8.4 g of 3-(2,2-dichlorovinyloxy)-α-cyanobenzyl cis, trans-2,2-dimethyl-3-(2,2,2-trichloroethyl) cyclopropanecarboxylate [Compound (34)] having the following NMR spectrum [yield: 88% based on the 3-(2,2-dichlorovinyloxy) benzaldehyde].

NMR spectrum (90 MHz) $\delta_{HMS}^{CDCl_3}$: 1.25, 1.28, 1.31, 1.35(each s)6H; 1.50–2.03(m)2H; 2.51–3.29(m)2H; 6.42, 6.45 (each s)1H; 6.89–7.60(m)5H.

SYNTHESIS EXAMPLES 9 TO 14

The procedure described in Synthesis Example 8 was repeated, except that 3-(4-chlorophenoxy) benzaldehyde, 3-(4-bromophenoxy) benzaldehyde, 3-(4-methylphenoxy) benzaldehyde, 3-(3-trifluoromethylphenoxy) benzaldehyde, 4-phenoxy benzaldehyde or 2-phenoxy benzaldehyde was used, respectively, in lieu of 3-(2,2-dichlorovinyloxy) benzaldehyde. By these procedures were obtained the corresponding cis, trans-2,2-dimethyl-3-(2,2,2-trichloroethyl) cyclopropanecarboxylic acid esters [Compounds (15), (17), (19), (20), (23) and (25) ], respectively, in a not less than 85% yield. By preparative liquid chromatography, the cis- and trans-isomers, as well as a mixture thereof, were obtained. The NMR spectra of the carboxylic acid esters obtained above are shown in Table 2.

TABLE 2

| Compound No. | | NMR spectrum (90 MHz) $\delta_{HMS}^{CDCl_3}$: |
|---|---|---|
| (15) | Cis-isomer: | 1.14, 1.17, 1.22(each s)6H; 1.41–1.89(m)2H; 2.72–3.29(m)2H; 6.30(s)1H; 6.78–7.48(m)8H |
| | Trans-isomer: | 1.16, 1.19, 1.28(each s)6H; 1.50(d)1H; 1.62–1.98(m)1H; 2.42–3.02(m)2H; 6.38(s)1H; 6.78–7.48(m)8H |
| (17) | Cis-isomer: | 1.14, 1.16, 1.18, 1.20(each s)6H; 1.41–1.89(m)2H; 2.70–3.28(m)2H; 6.30(s)1H; 6.71–7.51(m)8H |
| | Trans-isomer: | 1.14, 1.17, 1.25(each s)6H; 1.48(d)1H; 1.58–1.93(m)1H; 2.41–3.00(m)2H; 6.37(s)1H; 6.72–7.50(m)8H |
| (19) | Trans-isomer: | 1.20, 1.21, 1.24, 1.32(each s)6H; 1.54(d)1H; 1.68–2.04(m)1H; 2.36(s)3H; 2.47–3.06(m)2H; 6.40, 6.42(each s)1H; 6.83–7.48(m)8H |
| (20) | Trans-isomer: | 1.20, 1.22, 1.30(each s)6H; 1.56(d)1H; 1.70–2.03(m)1H; 2.48–3.06(m)2H; 6.45(s)1H; 7.00–7.62(m)8H |
| (23) | Trans-isomer: | 1.14, 1.20, 1.21, 1.27(each s)6H; 1.48(d)1H; 1.65–2.02(m)1H; 2.41–2.98(m)2H; 6.37(s)1H; 6.83–7.50(m)9H |
| (25) | Mixture: | 1.03–1.34(m)6H; 1.41–1.99(m)2H; 2.41–3.18(m)2H; 6.76–7.80(m)10H |

SYNTHESIS EXAMPLE 15

Into 215 g of toluene were dissolved 60.1 g of 3,3-dimethyl-4,6,6,6-tetrachlorohexanoyl chloride, followed by the addition of 127 g of pyridine. The mixture was heated under reflux for 5 hours. The reaction mixture was then allowed to stand and cool, after which 44.8 g of 3-phenoxy-α-ethynylbenzyl alcohol was added. The mixture was then stirred at room temperature overnight. The resultant reaction mixture was diluted with diethyl ether, washed with water and dilute hydrochloric acid, dried over anhydrous magnesium sulfate and distilled to remove the low-boiling fraction. The resultant oily residue was purified by preparative liquid chromatography to obtain 70.5 g of 3-phenoxy-α-ethynylbenzyl cis, trans-2,2-dimethyl-3-(2,2,2-trichloroethyl)cyclopropanecarboxylate [Compound (11)] (yield: 78%). The cis- and trans-isomers were separated from each other by the above preparative liquid chromatography. The NMR spectra of these isomers are shown below.

NMR spectrum (90 MHz) $\delta_{HMS}^{CDCl_3}$: Cis-isomer: 1.13, 1.14, 1.15, 1.20(each s)6H, 1.32–1.74(m)2H; 2.45–2.58(m)1H; 2.74–3.30(m)2H; 6.32–6.43(m)1H; 6.79–7.42(m)9H. Trans-isomer: 1.08, 1.12, 1.14, 1.24(each s)6H; 1.43(d)1H; 1.57–1.90(m)1H; 2.37–2.94(m)3H; 6.37–6.48(m)1H; 6.78–7.41(m)9H.

SYNTHESIS EXAMPLES 16 to 19

The procedure described in Synthesis Example 15 was repeated, except that 3-phenoxybenzyl alcohol, 3-(4-chlorophenoxy)-α-ethynylbenzyl alcohol, 3-(4-bromophenoxy)-α-ethynylbenzyl alcohol or 3-(2,2-dichlorovinyloxy) benzyl alcohol was used, respectively, in lieu of 3-phenoxy-6O-ethynylbenzyl alcohol. By these procedures were obtained the corresponding cis, trans-2,2-dimethyl-3-(2,2,2-trichloroethyl)cyclopropanecarboxylic acid esters [Compounds (1), (21), (22) and (33)], respectively, in a not less than 75% yield. By preparative liquid chromatography, the cis- and trans-isomers, as well as a mixture thereof, were obtained. The NMR spectra of the carboxylic acid esters obtained above are shown in Table 3.

TABLE 3

| Compound No. | | NMR spectrum (90 MHz) $\delta_{HMS}^{CDCl_3}$: |
|---|---|---|
| (1) | Cis-isomer: | 1.24, 1.25(each s)6H; 1.38–1.82(m)2H; 2.95(dd), 3.21(dd)2H; 5.06(s)2H; 6.84–7.46(m)9H |
| | Trans-isomer: | 1.15, 1.25(each s)6H; 1.50(d)1H; 1.82(q)1H; 2.63(dd), 2.85(dd)2H; 5.10(s)2H; 6.83–7.67(m)9H |
| (21) | Cis-isomer: | 1.22, 1.25, 1.27(each s)6H; 1.38–1.83(m)2H; 2.55–2.67(m)1H; 2.80–3.36(m)2H; 6.39–6.48(m)1H; 6.84–7.48(m)8H |
| | Trans-isomer: | 1.18, 1.20, 1.30(each s)6H; 1.52(d)1H; 1.63–1.98(m)1H; 2.47–3.04(m), 2.63(d)3H; 6.46(d)1H; 6.85–7.48(m)8H |
| (22) | Cis-isomer: | 1.22, 1.25, 1.27(each s)6H; 1.38–1.84(m)2H; 2.55–2.67(m)1H; 2.80–3.37(m)2H; 6.38–6.48(m)1H; 6.80–7.55(m)8H |
| | Trans-isomer: | 1.18, 1.23, 1.30(each s)6H; 1.54(d)1H; 1.68–1.98(m)1H; 2.49–3.04(m), 2.64(d)3H; 6.47(d)1H; 6.79–7.59(m)8H |
| (33) | Cis-isomer: | 1.20(s)6H; 1.34–1.78(m)2H; 2.93(dd), 3.15(dd)2H; 5.02(s)2H; 6.82–7.40(m)5H |
| | Trans-isomer: | 1.17, 1.24(each s)6H; 1.49(d)1H; 1.78(q)1H; 2.60(dd), 2.84(dd)2H; 5.07(s)2H; 6.83–7.40(m)5H |

SYNTHESIS EXAMPLE 20

Into 61 g of benzene were dissolved 27.3 g of 3,3-dimethyl-4,6,6,6-tetrabromohexanoyl chloride, followed by the addition of 36.1 g of pyridine. The mixture was heated under reflux for one hour. The reaction mixture was then allowed to stand and cool, after which 12.8 g of 3-phenoxy-α-ethynylbenzyl alcohol alcohol was added. The mixture was then stirred at room temperature overnight. The resultant reaction mixture was diluted with diethyl ether, washed with water and dilute hydrochloric acid, dried over anhydrous magnesium sulfate and distilled to remove the low-boiling fraction. The resultant oily residue was purified by preparative liquid chromatography to obtain 9.2 g of 3-phenoxy-α-ethynylbenzyl cis, trans-2,2-dimethyl-3-(2,2-tribromoethyl)cyclopropanecarboxylate [Compound (12)] (yield: 28%). The cis- and trans-isomers were separated from each other by preparative liquid chromatography. The NMR spectra of these isomers are shown below.

NMR spectrum (90 MHz) $\delta_{HMS}^{CDCl_3}$: Cis-isomer: 1.12, 1.13, 1.18(each s)6H; 1.30–1.85(m)2H; 2.47–2.60(m)1H; 2.94–3.62(m)2H; 6.32–6.43(m)1H; 6.77–7.40(m)9H. Trans-isomer: 1.09, 1.11, 1.17, 1.24(each s)6H; 1.50(d), 1.56–1.89(m)2H; 2.49–2.56(m)1H; 2.65–3.23(m)2H; 6.38–6.43(m)1H; 6.78–7.39(m)9H.

SYNTHESIS EXAMPLE 21

The procedure described in Synthesis Example 20 was repeated, by replacing the 3-phenoxy-α-ethynylbenzyl alcohol with 3-phenoxybenzyl alcohol. By this procedure there was obtained 3-phenoxybenzyl cis, trans-2,2-dimethyl-3-(2,2,2-tribromoethyl)cyclopropanecarboxylate [Compound (4)] in a 25% yield. By preparative liquid chromatography was separated the trans-isomer. The NMR spectrum of the trans-isomer is shown below.

NMR spectrum (90 MHz) $\delta_{HMS}^{CDCl_3}$: Trans-isomer: 1.15, 1.22(each s)6H; 1.50(d)1H; 1.73(q)1H; 2.87(dd), 3.14(dd)2H; 5.04(s)2H; 6.78–7.36(m)9H.

SYNTHESIS EXAMPLE 22

Into 20 ml of N,N-dimethylformamide were dissolved 2.50 g of 3-phenoxy-α-cyanobenzyl cis-2,2-dimethyl-3-(2,2,2-trichloroethyl)cyclopropanecarboxylate and 1 ml of triethanolamine, and hydrogen sulfide gas was bubbled into the solution at room temperature over a period of 15 hours. The resultant reaction mixture was poured into 500 ml of water and extracted with diethyl ether. The ethereal layer was washed with water, dried over anhydrous magnesium sulfate and distilled to remove diethyl ether. By the above procedure there were obtained 2.63 g of 3-phenoxy-α-thiocarbamoylbenzyl cis-2,2-dimethyl-3-(2,2,2-trichloroethyl)cyclopropanecarboxylate [Compound (27)] having the NMR spectrum shown hereinbelow (yield: 98%)

The procedure described above was repeated, by replacing 2.50 g 3-phenoxy-α-cyanobenzyl cis-2,2-dimethyl-3-(2,2,2-trichloroethyl)cyclopropanecarboxylate with 2.50 g of 3-phenoxy-α-cyanobenzyl trans-2,2-dimethyl-3-(2,2,2-trichloroethyl)cyclopropanecarboxylate. By this procedure there were obtained 2.66 g of 3-phenoxy-α-thiocarbamoylbenzyl trans-2,2-dimethyl-3-(2,2,2-trichloroethyl)cyclopropanecarboxylate [Compound (27)] having the following NMR spectrum (yield: 99%).

NMR spectrum (90 MHz) $\delta_{HMS}^{CDCl_3}$: Cis-isomer: 1.08, 1.16, 1.21(each s)6H; 1.37–1.84(m)2H; 2.72–3.30(m)2H; 6.35(s)1H; 6.79–7.42(m)9H; 7.65, 8.10(each bs)2H. Trans-isomer: 1.20, 1.22, 1.27(each s)6H; 1.43–1.95(m)2H; 2.47–3.04(m)2H; 6.44(s)1H; 6.87–7.47(m)9H; 7.73, 8.20(each bs)2H.

SYNTHESIS EXAMPLE 23

A pressure-resistant tubular reactor was charged with a mixture of 98.6 g of 3,3-dimethyl-4-pentenoic acid, 410 g of 1,1.1-trichloroethane and 4.6 g of t-butyl perbenzoate and, after the reactor was sealed, the contents were heated overnight at a temperature of 120° C., to 130° C., in an oil bath. Thereafter, the reaction mixture was distilled to recover the unreacted 1,1,1-trichloroethane and 3,3-dimethyl-4-pentenoic acid. By the above procedure there were obtained 38.5 g of the oily residue. This oily residue was dissolved in a mixture of 93 g of thionyl chloride and 120 g of benzene, and the mixture was heated under reflux overnight. The reaction mixture was then distilled under reduced pressure to remove the low-boiling fraction. The resultant residue was purified by distillation under reduced pressure to obtain 21.0 g of 3,3-dimethyl-4,6,6-trichloroheptanoyl chloride having the following NMR spectrum (yield: 10% based on the 3,3-dimethyl-4-pentenoic acid).

NMR spectrum (90 MHz) $\delta_{TMS}{}^{CDCl_3}$: 1.09, 1.22(each s)6H; 2.23(s)3H; 2.35–3.41(m)4H; 4.23(d), 4.24(d)1H.

Into 26.9 g of toluene were dissolved 7.0 g of the 3,3-dimethyl-4,6,6-trichloroheptanoyl chloride, followed by the addition of 15.8 g of pyridine. The mixture was heated under reflux for three hours. The resultant reaction mixture was then allowed to stand and cool, after which 3.9 g of 3-phenoxy-α-ethynylbenzyl alcohol was added. The mixture was then stirred at room temperature overnight. The reaction mixture was diluted with diethyl ether, washed with water and dilute hydrochloric acid, dried over anhydrous magnesium sulfate and distilled to remove the low-boiling fraction. The resultant oily residue was purified by preparative liquid chromatography to obtain 6.2 g of 3-phenoxy-α-ethynylbenzyl cis, trans-2,2-dimethyl-3-(2,2-dichloropropyl)cyclopropanecarboxylate [Compound (13)] (yield: 83% based on the 3-phenoxy-α-ethynylbenzyl alcohol). The cis- and trans-isomers were separated from each other by preparative liquid chromatography. The NMR spectra of these isomers are shown below.

NMR spectrum (90 MHz) $\delta_{HMS}{}^{CDCl_3}$: Cis-isomer: 1.17, 1.20, 1.23(each s)6H; 1.35–1.73(m)2H; 2.03, 2.14(each s)3H; 2.28–2.86(m)3H; 6.36–6.47(m)1H; 6.86–7.47(m)9H. Trans-isomer: 1.06, 1.08, 1.13, 1.20(each s)6H; 1.33(d)1H; 1.41–1.83(m)1H; 1.88–2.49(m)5H; 2.53(d)1H; 6.40(d)1H; 6.80–7.39(m)9H.

SYNTHESIS EXAMPLE 24

The procedure described in Synthesis Example 23 was repeated, by replacing the 3-phenoxy-α-ethynylbenzyl alcohol with 3-phenoxy-α-cyanobenzyl alcohol. By this procedure there was obtained 3-phenoxy-α-cyanobenzyl cis, trans-2,2-dimethyl-3-(2,2-dichloropropyl)cyclopropanecarboxylate [Compound (9)] in a 83% yield. By preparative liquid chromatography, the cis- and trans-isomers were separated from each other. The NMR spectra of these isomers are shown below.

NMR spectrum (90 MHz) $\delta_{HMS}{}^{CDCl_3}$: Cis-isomer: 1.18, 1.20, 1.24(each s)6H; 1.51–1.82(m)2H; 2.05, 2.17(each s)3H; 2.40–2.72(m)2H; 6.34(s)1H; 6.94–7.50(m)9H.

NMR spectrum (90 MHz) $\delta_{HMS}{}^{CDCl_3}$: Trans-isomer: 1.16, 1.19, 1.21, 1.30(each s)6H; 1.45(d)1H; 1.60–1.92(m)1H; 2.05–2.59(m)5H; 6.41(s)1H; 6.94–7.50(m)9H.

SYNTHESIS EXAMPLE 25

To 473 g of bromoform were added 60.0 g of ethyl 3,3-dimethyl-4-pentenoate and 4.0 g of benzoylperoxide, and the mixture was heated under reflux for 8 hours. The reaction mixture was then distilled under reduced pressure to recover 46.1 g of fraction having a boiling point of 148°–155° C./1.5 mm Hg. This fraction was dissolved in 450 ml of dry benzene. Then, 25.2 g of potassium t-butylate were added gradually to the above solution at 17° C. over a period of about 4 hours in an atmosphere of nitrogen and the mixture was further stirred at the same temperature for 30 minutes. The reaction mixture was then washed with ice water, dilute hydrochloric acid and water, dried over anhydrous magnesium sulfate and distilled to remove the low-boiling fraction. The resultant residue was further distilled under reduced pressure of 0.6 mm Hg to remove fraction of up to 90° C. and obtain 14.6 g of the residue. To a solution of 3.6 g of sodium hydroxide in 40 ml of water was added 14.6 g of the above residue, followed by the addition of about 50 ml of ethanol. The mixture was stirred at room temperature for one day. The reaction mixture was distilled under reduced pressure to remove ethanol and extracted with diethyl ether. The alkaline aqueous solution was made acidic by the addition of hydrochloric acid and extracted with diethyl ether to recover 12.0 g of crude 2,2-dimethyl-3-(2,2-dibromoethyl)cyclopropanecarboxylic acid. To 12.0 g of the above crude 2,2-dimethyl-3-(2,2-dibromoethyl)cyclopropanecarboxylic acid were added 28 g of thionyl chloride and 40 ml of benzene. The mixture was heated under reflux overnight. The reaction mixture was distilled under reduced pressure to remove the low-boiling fraction. The resultant residue was dissolved in 80 ml of dry benzene, and 9.0 g of 3-phenoxy-α-ethynylbenzyl alcohol were added. This was followed by the addition of 9.5 g of pyridine and the mixture was stirred at room temperature overnight. The resultant reaction mixture was diluted with diethyl ether, washed with dilute hydrochloric acid and saturated sodium chloride and dried over anhydrous magnesium sulfate. The low-boiling fraction was then distilled off and the residue was purified by preparative liquid chromatography to obtain 5.3 g of 3-phenoxy-α-ethynylbenzyl trans-2,2-dimethyl-3-(2,2-dibromoethyl)cyclopropanecarboxylate [Compound (14)] having the following NMR spectrum.

NMR spectrum (90 MHz) $\delta_{HMS}{}^{CDCl_3}$: Trans-isomer: 1.06, 1.09, 1.12, 1.20(each s)6H; 1.28–1.66(m)2H; 2.16–2.57(m)3H; 5.44–5.71(m)1H; 6.35–6.43(m)1H; 6.78–7.37(m)9H.

TEST EXAMPLE 1

Mortality test against houseflies by topical application

Each test compound was accurately weighed and a 1% solution and an 0.1% solution of the sample in acetone were prepared. A 1 μl portion of either of the above solutions was micropipetted onto the thoracic dorsal part of each female adult housefly (*Musca domestica*) under ether anaesthesia and the fly was released in a high-walled dish together with feed. The dish was covered with a metal-wire net and maintained at 25° C. After 24 hours, the test flies were inspected for deaths and the mortality (%) was calculated. The results are set forth in Table 4. Thirty test flies were used per concentration group.

TABLE 4

| Test Compound No. | Mortality (%) | |
|---|---|---|
| | 10μg/fly | 1μg/fly |
| (1) [Cis-isomer] | 100 | 96.7 |
| (2) [Mixture] | 86.7 | 0 |
| (5) [Mixture] | 100 | 100 |
| (7) [Trans-isomer] | 100 | 96.7 |
| (9) [Mixture] | 100 | 100 |
| (11) [Trans-isomer] | 100 | 100 |
| (15) [Mixture] | 100 | 86.7 |
| (21) [Mixture] | 93.3 | 60 |
| (28) [Mixture] | 100 | 86.7 |
| (33) [Mixture] | 33.3 | 6.7 |
| (34) [Mixture] | 100 | 56.7 |
| (37) [Mixture] | 56.7 | 40 |
| (38) [Mixture] | 100 | 6.7 |
| Allethrin | 100 | 33.3 |

Note: [Mixture] means a ratio of cis/trans = 50/50

TEST EXAMPLE 2

Mortality test against green rice leafhoppers by topical application

Each test compound was accurately weighed and each acetone solution containing one of the test compounds in a predetermined concentration was prepared. Female adults of green rice leafhopper (*Nephotettix cincticeps*) acquiring resistance to the common pesticides comprising the organic phosphorus compounds and the carbamates were anaesthetized with carbon dioxide gas and 0.5 μl of the above solution was micropipetted onto the thoracic abdominal part of each leafhopper. Then, the test leafhoppers were kept at 25° C. with access to rice plant seedlings. Each group comprised 15 green rice leafhoppers. After 24 hours, the leafhoppers were inspected for deaths and an $LD_{50}$ (50% lethal dose) was determined by calculating a percent mortality in each case. The results are set forth in Table 5.

TABLE 5

| Test Compound No. | $LD_{50}$ (μg/g) |
|---|---|
| (7) [Mixture] | 1.90 |
| (11) [Trans-isomer] | 1.37 |
| [Cis-isomer] | 3.15 |
| [Mixture] | 2.82 |
| (12) [Mixture] | 4.46 |
| (15) [Mixture] | 4.89 |
| (21) [Mixture] | 4.72 |
| (22) [Mixture] | 8.86 |
| (28) [Mixture] | not less than 14 |
| (37) [Mixture] | not less than 14 |
| (38) [Mixture] | not less than 14 |
| Diazinon | 45.5 |
| Malathion | 606.5 |
| Tsumacide | 70.1 |
| Carbaryl | 39.8 |

Note: [Mixture] means a ratio of cis/trans = 50/50.

TEST EXAMPLE 3

Light stability test

Into 2.0 ml of acetone were dissolved 80 mg of each test compound. A 5 μl portion of the solution was taken and spread on a glass plate (Micro Standard Cover Glass, 18 m/m No. 1, 200 pcs, Matsunami Glass Ind., Ltd.) and the acetone was evaporated. The specimen was exposed to ultraviolet light from a fluorescent lamp (Tokyo Shibaura Electric Co., Ltd., FL20BL, glow-type, 100 V, 24.5 W, wavelength=3600 Å) which was fixed just above the specimen at a distance of 11 cm at a temperature of 31°–35° C. for a predetermined exposure time. The test liquid was washed away with 1.0 ml of methanol containing 0.04% of dioctyl phthalate as an internal reference and high-speed liquid chromatography was carried out on the washings to determine the residual amount of the test compound. The percent residue (%) is shown in Table 6.

TABLE 6

| Test Compound No. | Residue (%) Exposure time | | |
|---|---|---|---|
| | 3.5 hours | 3 days | 5 days |
| (1) [Cis-isomer] | 97 | 91 | 85 |
| (7) [Mixture] | 100 | 84 | 75 |
| (11) [Mixture] | 100 | 71 | 65 |
| (13) [Cis-isomer] | 100 | 88 | 73 |
| (15) [Mixture] | 100 | 93 | 96 |
| (21) [Mixture] | 100 | 78 | 56 |
| (28) [Mixture] | 5 | 0 | — |

TABLE 6-continued

| Test Compound No. | Residue (%) Exposure time | | |
|---|---|---|---|
| | 3.5 hours | 3 days | 5 days |
| (34) [Mixture] | 100 | 88 | 44 |
| (37) [Mixture] | 16 | 0 | — |
| (38) [Mixture] | 21 | 0 | — |
| Allethrin | 14 | 0 | — |

Note: [Mixture] means a ratio of cis/trans = 50/50.

TEST EXAMPLE 4

Fish toxicity test

To 5 l of water were added 250 mg of Sorpol SM-200 (registered trademark, Toho Chemical Co., Ltd.) as an emulsifier (surfactant) as well as 2.5 ml of an acetone solution containing one of the test compounds in a predetermined concentration. The mixture was stirred well to prepare a test water. Ten female guppies from 3 to 4 months of age were released into the test water and maintained at 20° C. The concentration of the test compound at which 50% of the guppies were killed during the ensuring 48 hours was determined. [This concentration is referred to as TLm (medium tolerance limit, ppm)]. The results were judged by the following rank and set forth in Table 7.

A rank corresponds to TLm of not less than 10 ppm.
B rank corresponds to TLm of 0.5–10 ppm.
C rank corresponds to TLm of not more than 0.5 ppm.

TABLE 7

| Test Compound No. | TLm |
|---|---|
| (1) [Cis-isomer] | A |
| (2) [Mixture] | A |
| (7) [Trans-isomer] | B |
| [Mixture] | B |
| (11) [Trans-isomer] | A |
| (12) [Mixture] | A |
| (13) [Cis-isomer] | A |
| (15) [Mixture] | A |
| (21) [Mixture] | A |
| (27) [Cis-isomer] | A |
| (28) [Mixture] | A |
| (33) [Mixture] | A |
| (34) [Mixture] | A |
| (37) [Mixture] | B |
| (38) [Mixture] | B |
| Allethrin | C |
| Resmethrin | C |
| Permethrin | C |
| Cypermethrin | C |
| Fenvalerate | C |

Note: [Mixture] means a ratio of cis/trans = 50/50.

FORMULATION EXAMPLE 1

0.2 part of each of Compounds (1) to (38) was prepared and 0.8 part of piperonyl butoxide was added to each of them. To this mixture was added a sufficient amount of kerosene to make 100 parts, followed by stirring. By this procedure there was obtained an oil preparation of each Compound.

FORMULATION EXAMPLE 2

To 0.1 part of each of Compounds (1) to (38) was added 0.1 part of resmethrin, followed by the addition of a sufficient amount of kerosene to make 100 parts. The mixture was stirred to obtain an oil preparation of each compound.

FORMULATION EXAMPLE 3

To 0.1 part of each of Compounds (1) to (38) was added 0.08 part of permethrin, followed by the addition of a sufficient amount of kerosene to make 100 parts. The mixture was stirred to obtain an oil preparation of each compound.

FORMULATION EXAMPLE 4

To 0.2 part of each of Compounds (1) to (38) was added 0.2 part of 2-isopropoxyphenyl N-methylcarbamate and 5 parts of xylene. The composition was dissolved in a sufficient amount of kerosene to make 100 parts. In the above manner, an oil preparation of each compound was obtained.

FORMULATION EXAMPLE 5

To 30 parts of each of Compounds (1) to (38) were added 50 parts of xylene and 20 parts of Sorpol SM-200 (a surfactant, trademark of Toho Chemical Co., Ltd.). The mixture was stirred well and dissolved to obtain a 30% emulsifiable concentrate.

FORMULATION EXAMPLE 6

To 20 parts of each of Compounds (1) to (38) were added 20 parts of O,O-dimethyl-O-4-cyanophenyl phosphorothioate [Thianox, trademark of Sumitomo Chemical Co., Ltd.], 20 parts of Sorpol SM-200 (a surfactant, trademark of Toho Chemical Co., Ltd.) and 40 parts of xylene. The mixture was stirred well to effect dissolution, whereby an emulsifiable concentrate of each compound was obtained.

FORMULATION EXAMPLE 7

To 20 parts of each of Compounds (1) to (38) were added 5 parts of Sorpol SM-200 (a surfactant, trademark of Toho Chemical Co. Ltd.), followed by thorough mixing. With the addition of 75 parts of 300-mesh talc, the mixture was thoroughly stirred in a triturator. By the above procedure there was obtained a wettable powder of each compound.

FORMULATION EXAMPLE 8

To 15 parts of each of Compounds (1) to (38) were added 15 parts of 1-naphthyl N-methylcarbamate and 5 parts of Sorpol SM-200 (a surfactant, trademark of Toho Chemical Co., Ltd.), followed by thorough mixing. With the addition of 65 parts of 300-mesh talc, the mixture was thoroughly stirred in a triturator to obtain a wettable powder of each compound.

FORMULATION EXAMPLE 9

To one part of each of Compounds (1) to (38) were added 5 parts of piperonyl butoxide and the mixture was dissolved in 20 parts of acetone. With the addition of 94 parts of 300-mesh diatomaceous earth, the mixture was stirred well and mixed in a triturator and the acetone was evaporated off. By the above procedure there was obtained a powder containing each compound.

FORMULATION EXAMPLE 10

To 0.4 part of each of Compounds (1) to (38) was added 0.1 part of resmethrin, 1.5 parts of octachlorodipropyl ether and 28 parts of refined kerosene. The solution thus obtained was dispensed into aerosol containers and, after the valve was attached, each container was filled with 70 parts of propellant (liquefied petroleum gas). By this procedure there was obtained an aerosol preparation of each compound.

FORMULATION EXAMPLE 11

To 0.3 part of each of Compounds (1) to (38) was added 0.3 part of DDVP and the mixture was dissolved in a mixture of xylene and refined kerosene to make a total of 15 parts. Each solution was dispensed into aerosol containers and, after the valve was attached, each container was filled with 85 parts of a propellant (liquefied petroleum gas) through the filling valve. By the above procedure there was obtained an aerosol preparation of each compound.

FORMULATION EXAMPLE 12

To 0.5 part of each of Compounds (1) to (38) was added 0.5 part of BHT and 99.0 parts of mosquito incense coil materials including pyrethrum marc, sawdust, starch, etc. The mixture was evenly blended and processed into a mosquito coil in a manner conventional, per se.

FORMULATION EXAMPLE 13

To 0.05 g of each of Compounds (1) to (38) was added 0.02 g of furamethrin, 0.15 g of piperonyl butoxide and 0.1 g of BHT and the mixture was dissolved in an appropriate amount of chloroform. This solution was adsorbed uniformly on the surface of an asbestos mat having a size of 2.5 cm × 1.5 cm and a thickness of 0.3 mm, and another asbestos mat of the same size and thickness was superimposed on the treated surface. By this procedure there was obtained a fibrous fumigation pesticidal composition (mat) for heating on a hot plate.

UTILITY EXAMPLE 1

The emulsifiable concentrate prepared from Compounds (7), (11), (12), (15), (17), (21) and (22) [Each compound is a mixture of cis- and trans-isomer in a ratio of 50/50] in Formulation Example 5 were each diluted 300-fold with water. Then, each of the dilutions was sprayed over rice seedlings 25 days after sowing at the rate of 10 ml/pot. The pot was covered with a wire net and 15 green rice leafhoppers were released under the net. After 24 hours, the leafhoppers were examined for deaths. The mortality (%) was not less than 90% for each of Compounds (7), (11), (12), (15), (17), (21) and (22).

UTILITY EXAMPLE 2

By the settling mist method, a mortality test against houseflies, (*Musca domestica*) was carried out using the oil preparations obtained according to Formulation Example 1 from Compounds (1), (5), (7), (9), (11) and (15) [Each compound is a mixture of cis- and trans-isomer in a ratio 50/50]. After 24 hours, the flies were examined for deaths. The mortality (%) was not less than 90% for each of Compounds (1), (5), (7), (9), (11) and (15).

UTILITY EXAMPLE 3

By the settling mist method, a mortality test against houseflies was carried out using the oil preparations obtained in Formulation Example 3 from Compounds (1), (5), (7), (9), (11), (12), (15), (17) and (28) [Each compound is a mixture of cis- and trans-isomer in a ratio 50/50]. After 24 hours, the flies were examined for deaths. The mortality (%) was not less than 90% for each of Compounds (1), (5), (7), (9), (11), (12), (15), (17) and (28).

UTILITY EXAMPLE 4

The emulsifiable concentrate prepared from Compounds (7), (11) and (15) [Each compound is a mixture of cis- and trans-isomer in a ratio 20/80] in Formulation Example 5 were each diluted 1000-fold with water. Each of 15 common cabbage worms (*Pieris rapae crucivora*) per group were dipped into each of the dilutions for three seconds. Then, the worms were released on the leaves of the cabbage. After 24 hours, the worms were examined for deaths. The mortality (%) was not less than 90% for each of Compounds (7), (11) and (15).

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A method for the control of agricultural and horticultural insects, forest insects, harvested crop insects, household insects, mites, and pests of the genera Tetigoniidae, Gryllidae, Gryllotalpidae, Blattidae, Reduviidae, Pyrrhocoridae, Cimicidae, Delphacidae, Aphididae, Diaspididae, Pseudococcidae, Scarabaeidae, Dermestidae, Coccinellidae, Tenebrionidae, Chrysomelidae, Bruchidae, Tineidae, Noctuidae, Lymantriidae, Pyralidae, Culicidae, Tipulidae, Stomoxydae, Trypetidae, Muscidae, Calliphoridae, Pulicidae, Tetranychidae and Dermanyssidae, which comprises applying to the habitat of such pests a pesticidally effective amount of a cyclopropanecarboxylate having the structural formula:

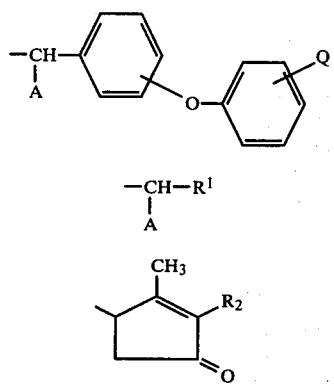

wherein X, Y and Z are the same or different and at least two of same are chlorine or bromine, with the remaining one being hydrogen, methyl, chlorine or bromine; R is a member selected from the group consisting of those of the structural formulae (1), (2) and (3):

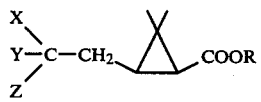

(1)

—CH—R¹
|
A (2)

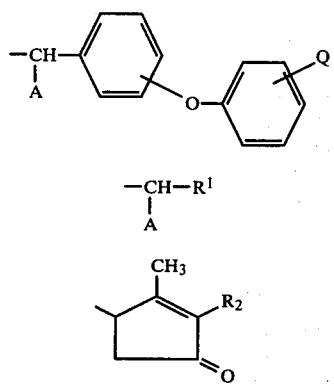

(3)

where A is hydrogen, cyano, ethynyl or thiocarbamoyl; Q is hydrogen, chlorine, bromine, fluorine, methyl or trifluoromethyl; R¹ is 2-halogeno-3-phenyl-1-propen-1-yl, (dihalogenovinyloxy)phenyl or benzylphenyl; and R² is allyl, 2,4-pentadienyl, propargyl or benzyl.

2. The method as defined by claim 1, wherein R has the structural formula (1).

3. The method as defined by claim 1, wherein R has the structural formula (2).

4. The method as defined by claim 1, wherein R has the structural formula (3).

5. The method as defined by claim 1, the cyclopropanecarboxylate having the structural formula:

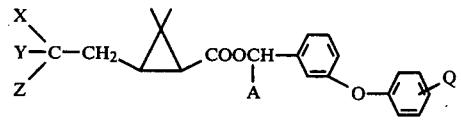

wherein X, Y and Z are the same or different and at least two of same are chlorine or bromine, with the remaining being hydrogen, methyl, chlorine or bromine; A is hydrogen, cyano, ethynyl or thiocarbamoyl; and Q is hydrogen, chlorine, bromine, fluorine, methyl or trifluoromethyl.

6. The method as defined by claim 5, the cyclopropanecarboxylate having the structural formula:

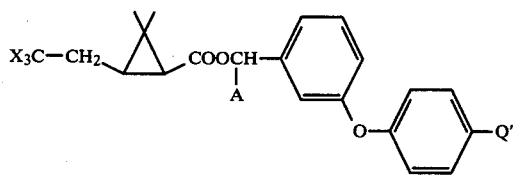

wherein each X, which may be the same or different, is chlorine or bromine; A is hydrogen, cyano, ethynyl or thiocarbamoyl; and Q' is hydrogen, chlorine or bromine.

7. The method as defined by claim 1, the cyclopropanecarboxylate having the structural formula:

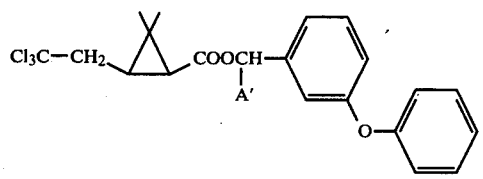

wherein A' is cyano or ethynyl.

8. The method as defined by claim 7, wherein A' is cyano.

9. The method as defined by claim 7, wherein A' is ethynyl.

10. The method as defined by claim 2, wherein A is hydrogen.

11. The method as defined by claim 2, wherein A is cyano.

12. The method as defined by claim 2, wherein A is ethynyl.

13. The method as defined by claim 2, wherein A is thiocarbamoyl.

14. The method as defined by claims 2, 11 or 12, wherein Q is chlorine.

15. The method as defined by claims 2, 11 or 12, wherein Q is bromine.

16. The method as defined by claims 2, 11 or 12, wherein Q is fluorine.

17. The method as defined by claims 2, 11 or 12, wherein Q is trifluoromethyl.

18. The method as defined by claim 3, wherein A is hydrogen.

19. The method as defined by claim 3, wherein A is cyano.

20. The method as defined by claim 3, wherein A is ethynyl.

21. The method as defined by claim 3, wherein A is thiocarbamoyl.

22. The method as defined by claims 3, 19 or 20, wherein $R^1$ is 2-halogen-3-phenyl-1-propen-1-yl.

23. The method as defined by claims 3, 19 or 20, wherein $R^1$ is (dihalogenovinyloxy)phenyl.

24. The method as defined by claims 3, 19 or 20, wherein $R^1$ is benzylphenyl.

25. The method as defined by claim 4, wherein $R^2$ is allyl.

26. The method as defind by claim 4, wherein $R^2$ is 2,4-pentadienyl.

27. The method as defined by claim 4, wherein $R^2$ is propargyl.

28. The method as defined by claim 4, wherein $R^2$ is benzyl.

29. The method as defined by claim 1, the cyclopropanecarboxylate being 3-phenoxybenzyl 2,2-dimethyl-3-(2,2,2-trichloroethyl)cyclopropanecarboxylate.

30. The method as defined by claim 1, the cyclopropanecarboxylate being 3-(4-chlorophenoxy)benzyl 2,2-dimethyl-3-(2,2,2-trichloroethyl)cyclopropanecarboxylate.

31. The method as defined by claim 1, the cyclopropanecarboxylate being 3-(4-bromophenoxy)benzyl 2,2-dimethyl-3-(2,2,2-trichloroethyl)cyclopropanecarboxylate.

32. The method as defined by claim 1, the cyclopropanecarboxylate being 3-phenoxybenzyl 2,2-dimethyl-3-(2,2,2-tribromomethyl)cyclopropanecarboxylate.

33. The method as defined by claim 1, the cyclopropanecarboxylate being 3-phenoxybenzyl 2,2-dimethyl-3-(2,2-dichloropropyl)cyclopropanecarboxylate.

34. The method as defined by claim 1, the cyclopropanecarboxylate being 3-phenoxybenzyl 2,2-dimethyl-3-(2,2-dibromoethyl)cyclopropanecarboxylate.

35. The method as defined by claim 1, the cyclopropanecarboxylate being 3-phenoxy-α-cyanobenzyl 2,2-dimethyl-3-(2,2,2-tribromoethyl)cyclopropanecarboxylate.

36. The method as defined by claim 1, the cyclopropanecarboxylate being 3-phenoxy-α-cyanobenzyl 2,2-dimethyl-3-(2,2-dichloropropyl)cyclopropanecarboxylate.

37. The method as defined by claim 1, the cyclopropanecarboxylate being 3-phenoxy-α-cyanobenzyl 2,2-dimethyl-3-(2,2-dibromomethyl)cyclopropanecarboxylate.

38. The method as defined by claim 1, the cyclopropanecarboxylate being 3-phenoxy-α-ethynylbenzyl 2,2-dimethyl-3-(2,2,2-tribromoethyl)cyclopropanecarboxylate.

39. The method as defined by claim 1, the cyclopropanecarboxylate being 3-phenoxy-α-ethynylbenzyl 2,2-dimethyl-3-(2,2-dichloropropyl)cyclopropanecarboxylate.

40. The method as defined by claim 1, the cyclopropanecarboxylate being 3-phenoxy-α-ethynylbenzyl 2,2-dimethyl-3-(2,2-dibromomethyl)cyclopropanecarboxylate.

41. The method as defined by claim 1, the cyclopropanecarboxylate being 3-(4-chlorophenoxy)-α-cyanobenzyl 2,2-dimethyl-3-(2,2,2-trichloroethyl)cyclopropanecarboxylate.

42. The method as defined by claim 1, the cyclopropanecarboxylate being 3-(4-chlorophenoxy)-α-cyanobenzyl 2,2-dimethyl-3-(2,2,2-tribromoethyl)cyclopropanecarboxylate.

43. The method as defined by claim 1, the cyclopropanecarboxylate being 3-(4-bromophenoxy)-α-cyanobenzyl 2,2-dimethyl-3-(2,2,2-trichloroethyl)cyclopropanecarboxylate.

44. The method as defined by claim 1, the cyclopropanecarboxylate being 3-(4-fluorophenoxy)-α-cyanobenzyl 2,2-dimethyl-3-(2,2,2-trichloroethyl)cyclopropanecarboxylate.

45. The method as defined by claim 1, the cyclopropanecarboxylate being 3-(4-methylphenoxy)-α-cyanobenzyl 2,2-dimethyl-3-(2,2,2-trichloroethyl)cyclopropanecarboxylate.

46. The method as defined by claim 1, the cyclopropanecarboxylate being 3-(3-trifluoromethylphenoxy)-α-cyanobenzyl 2,2-dimethyl-3-(2,2,2-trichloroethyl)cyclopropanecarboxylate.

47. The method as defined by claim 1, the cyclopropanecarboxylate being 3-(4-chlorophenoxy)-α-ethynylbenzyl 2,2-dimethyl-3-(2,2,2-trichloroethyl)cyclopropanecarboxylate.

48. The method as defined by claim 1, the cyclopropanecarboxylate being 3-(4-bromophenoxy)-α-ethynylbenzyl 2,2-dimethyl-3-(2,2,2-trichloroethyl)cyclopropanecarboxylate.

49. The method as defined by claim 1, the cyclopropanecarboxylate being 4-phenoxy-α-cyanobenzyl 2,2-dimethyl-3-(2,2,2-trichloroethyl)cyclopropanecarboxylate.

50. The method as defined by claim 1, the cyclopropanecarboxylate being 4-phenoxy-α-ethynylbenzyl 2,2-dimethyl-3-(2,2,2-trichloroethyl)cyclopropanecarboxylate.

51. The method as defined by claim 1, the cyclopropanecarboxylate being 2-phenoxy-α-cyanobenzyl 2,2-dimethyl-3-(2,2,2-trichloroethyl)cyclopropanecarboxylate.

52. The method as defined by claim 1, the cyclopropanecarboxylate being 2-phenoxy-α-ethynylbenzyl 2,2-dimethyl-3-(2,2,2-trichloroethyl)cyclopropanecarboxylate.

53. The method as defined by claim 1, the cyclopropanecarboxylate being 3-phenoxy-α-thiocarbamoylbenzyl 2,2-dimethyl-3-(2,2,2-trichloroethyl)cyclopropanecarboxylate.

54. The method as defined by claim 1, the cyclopropanecarboxylate being 3-chloro-4-phenyl-2-butenyl 2,2-dimethyl-3-(2,2,2-trichloroethyl)cyclopropanecarboxylate.

55. The method as defined by claim 1, the cyclopropanecarboxylate being 3-(2,2-dichlorovinyloxy)benzyl 2,2-dimethyl-3-(2,2,2-trichloroethyl)cyclopropanecarboxylate.

56. The method as defined by claim 1, the cyclopropanecarboxylate being 3-(2,2-dichlorovinyloxy)-α-cyanobenzyl 2,2-dimethyl-3-(2,2,2-trichloroethyl)cyclopropanecarboxylate.

57. The method as defined by claim 1, the cyclopropanecarboxylate being 3-(2,2-dichlorovinyloxy)-α- cyanobenzyl 2,2-dimethyl-3-(2,2,2-tribromoethyl)cyclopropanecarboxylate.

58. The method as defined by claim 1, the cyclopropanecarboxylate being 3-(2,2-dichlorovinyloxy)-α-cyanobenzyl 2,2-dimethyl-3-(2,2-dichloropropyl)cyclopropanecarboxylate.

59. The method as defined by claim 1, the cyclopropanecarboxylate being allethronyl 2,2-dimethyl-3-(2,2,2-trichloroethyl)cyclopropanecarboxylate.

60. The method as defined by claim 1, said pest habitat being an agricultural crop.

61. The method as defined by claim 1, said pest habitat being a horticultural crop.

62. The method as defined by claim 1, said pest habitat being a rice paddy field.

63. The method as defined by claim 1, said pest habitat being a domestic household.

64. The method as defined by claim 1, said pest habitat being a vegetable crop.

65. The method as defined by claim 1, said pest habitat being an orchard.

66. The method as defined by claim 1, said habitat being a flowering plant.

67. The method as defined by claim 1, said pest habitat being a cotton plant.

68. The method as defined by claim 1, said pest habitat being a stored crop.

69. A pesticidal composition of matter comprising (i) a pesticidally effective amount, effective against agricultural and horticultural insects, forest insects, harvested crop insects, household insects, mites, and pests of the genera Tettigoniidae, Gryllidae, Gryllotalpidae, Blattidae, Reduviidae, Pyrrhocoridae, Cimicidae, Delphacidae, Aphididae, Diasapididae, Pseudococcidae, Scarabaeidae, Dermestidae, Coccinellidae, Tenebrionidae, Chrysomelidae, Bruchidae, Tineidae, Noctuidae, Lymantriidae, Pyralidae, Culicidae, Tipulidae, Stomoxydae, Trypetidae, Muscidae, Calliphoridae, Pulicidae, Tetranychidae and Dermanyssidae, of a purified active cyclopropanecarboxylate having the structural formula:

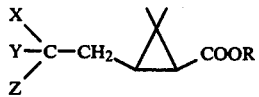

wherein X, Y and Z are the same or different and at least two of same are chlorine or bromine, with the remaining one being hydrogen, methyl, chlorine or bromine; R is a member selected from the group consisting of those of the structural formulae (1), (2) and (3):

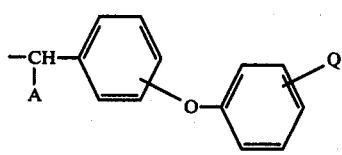 (1)

 (2)

-continued

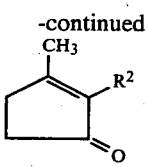 (3)

where A is hydrogen, cyano, ethynyl or thiocarbamoyl; Q is hydrogen, chlorine, bromine, fluorine, methyl or trifluoromethyl; $R^1$ is 2-halogeno-3-phenyl-1-propen-1-yl, (dihalogenovinyloxy)phenyl or benzylphenyl; and $R^2$ is allyl, 2,4-pentadienyl, propargyl or benzyl, formulated with (ii) a pesticidally acceptable inert carrier therefor, with said active cyclopropanecarboxylate/carrier pesticidal composition being formulated as a formulation selected from the group consisting of emulsifiable concentrate, wettable powder dust, granular, microfine granular, powder, aerosol, incense coil, fumigant, delayed release, incense mat, capsular and oil preparation.

70. The pesticidal composition as defined by claim 69, wherein R has the structural formula (1).

71. The pesticidal composition as defined by claim 69, wherein R has the structural formula (2).

72. The pesticidal composition as defined by claim 69, wherein R has the structural formula (3).

73. The pesticidal composition as defined by claim 69, formulated in the form of a wettable powder.

74. The pesticidal composition as defined by claim 69, formulated in the form of an emulsifiable concentrate.

75. The pesticidal composition as defined by claim 69, formulated in the form of a dust.

76. The pesticidal composition as defined by claim 69, formulated in the form of a powder.

77. The pesticidal composition as defined by claim 69, formulated in aerosol form.

78. The pesticidal composition as defined by claim 69, formulated in granular form.

79. The pesticidal composition as defined by claim 69, formulated in fumigant form.

80. The pesticidal composition as defined by claim 69, formulated in capsular form.

81. The pesticidal composition as defined by claim 69, including a surfactant.

82. The pesticidal composition as defined by claim 69, including a dispersing agent.

83. The pesticidal composition as defined by claim 69, including a foaming agent.

84. The pesticidal composition as defined by claim 69, wherein the inert carrier comprises a propellant gas.

85. The pesticidal composition as defined by claim 69, wherein the inert carrier comprises a solid.

86. The pesticidal composition as defined by claim 69, wherein the cyclopropanecarboxylate (i) is present in an amount of up to 95 weight percent.

87. The pesticidal composition as defined by claim 69, wherein the cyclopropanecarboxylate (i) is present in an amount of from 0.1 to 90 weight percent.

88. The pesticidal composition as defined by claim 69, wherein the cyclopropanecarboxylate (i) is present in an amount of from 0.001 to 10 weight percent.

89. The pesticidal composition as defined by claim 69, including an antioxidant.

90. The pesticidal composition as defined by claim 69, including an adhesive.

91. The pesticidal composition as defined by claim 69, including a colorant.

92. The pesticidal composition as defined by claim 85, including a member selected from the group consisting of finely divided kaolin, clay, talc, chalk, quartz, attapulgite, montmorillonite, and diatomaceous earth, and finely divided alumina and silica.

93. A method for the control of agricultural and horticultural insects, forest insects, harvested crop insects, household insects, mites, and pests of the genera Tettigoniidae, Gryllidae, Gryllotalpidae, Blattidae, Reduviidae, Pyrrhocoridae, Cimicidae, Delphacidae, Aphididae, Disapididae, Pseudococcidae, Scarabaeidae, Dermestidae, Coccinellidae, Tenebrionidae, Chrysomelidae, Bruchidae, Tineidae, Noctuidae, Lymantriidae, Pyralidae, Culicidae, Tipulidae, Stomoxydae, Trypetidae, Muscidae, Calliphoridae, Pulicidae, Tetranychidae and Dermanyssidae, which comprises applying to the habitat of such pests a pesticidally effective amount of the pesticidal composition of matter as defined by any of claims 69 to 72.

* * * * *